(12) United States Patent
Yohannes et al.

(10) Patent No.: US 6,861,529 B2
(45) Date of Patent: Mar. 1, 2005

(54) CYCLOALKYPYRROLE-3-CARBOXYLIC ACID DERIVATIVES AND HETEROCYCLOALKYLPYRROLE-3-CARBOXYLIC ACID DERIVATIVES

(75) Inventors: Daniel Yohannes, New London, CT (US); George Maynard, Clinton, CT (US); Xiaojun Liu, New London, CT (US)

(73) Assignees: Pfizer Inc, New York, NY (US); Neurogen Corporation, Clinton, CT (US)

( * ) Notice: Subject to any disclaimer, the term of this patent is extended or adjusted under 35 U.S.C. 154(b) by 55 days.

(21) Appl. No.: 10/131,329

(22) Filed: Apr. 24, 2002

(65) Prior Publication Data

US 2003/0069416 A1 Apr. 10, 2003

Related U.S. Application Data

(60) Provisional application No. 60/303,467, filed on Jul. 6, 2001.

(51) Int. Cl.[7] .................... C07D 471/02; C07D 221/02; C07D 211/60
(52) U.S. Cl. .................... 546/183; 546/227.1; 546/122; 546/199
(58) Field of Search .............................. 546/183, 227.1, 546/122, 199

(56) References Cited

U.S. PATENT DOCUMENTS

| | | | | |
|---|---|---|---|---|
| 5,023,265 A | * | 6/1991 | Scherlock et al. | 514/300 |
| 5,484,944 A | * | 1/1996 | Albaugh et al. | 546/171 |
| 5,608,079 A | * | 3/1997 | Albaugh et al. | 548/492 |
| 5,750,702 A | * | 5/1998 | Albaugh et al. | 546/183 |
| 5,925,770 A | * | 7/1999 | Albaugh et al. | 548/452 |

FOREIGN PATENT DOCUMENTS

| | | | |
|---|---|---|---|
| WO | WO 95/11885 | | 5/1995 |
| WO | WO 97/34870 | | 9/1997 |
| WO | WO 98/02420 | * | 1/1998 |
| WO | WO 01/16103 A1 | | 3/2001 |

OTHER PUBLICATIONS

Li, Organic Process Research & Developemnt, 2002, vol 6, pp. 64–66.*

* cited by examiner

*Primary Examiner*—D. Margaret Seaman
(74) *Attorney, Agent, or Firm*—Peter C. Richardson; Seth H. Jacobs; E. Victor Donahue

(57) ABSTRACT

This invention relates to cycloalkylpyrrole-3-carboxylic acid derivatives and heterocycloalkylpyrrole-3-carboxylic acid derivatives that bind with high selectively and/or high affinity to the benzodiazepine site of $GABA_A$ receptors. This invention also relates to pharmaceutical compositions comprising such compounds and to the use of such compounds in the treatment of central nervous system (CNS) diseases. This invention also relates to the use of these cycloalkylpyrrole-3-carboxylic acid derivatives and heterocycloalkylpyrrole-3-carboxylic acid derivatives in combination with one or more other CNS agents to potentiate the effects of the other CNS agents. Additionally this invention relates to the use such compounds as probes for the detection of $GABA_A$ receptors in tissue samples.

31 Claims, No Drawings

CYCLOALKYPYRROLE-3-CARBOXYLIC ACID DERIVATIVES AND HETEROCYCLOALKYLPYRROLE-3-CARBOXYLIC ACID DERIVATIVES

This application claims benefit to U.S. Provisional Application No. 60/303,467 filed Jul. 6, 2001.

FIELD OF THE INVENTION

This invention relates to a certain cycloalkylpyrrole-3-carboxylic acid derivatives and heterocycloalkylpyrrole-3-carboxylic acids derivatives that bind with high selectively and/or high affinity to the benzodiazepine site of $GABA_A$ receptors. This invention also relates to pharmaceutical compositions comprising such compounds and to the use of such compounds in the treatment of central nervous system (CNS) diseases. This invention also relates to the use of these cycloalkylpyrrole-3-carboxylic acid derivative and heterocycloalkylpyrrole-3-carboxylic acids derivative compounds in combination with one or more other CNS agents to potentiate the effects of the other CNS agents. Additionally this invention relates to the use such compounds as probes for the localization of $GABA_A$ receptors in tissue sections.

BACKGROUND

The $GABA_A$ receptor superfamily represents one of the classes of receptors through which the major inhibitory neurotransmitter, γ-aminobutyric acid, or GABA, acts. Widely, although unequally, distributed throughout the mammalian brain, GABA mediates many of its actions through a complex of proteins called the $GABA_A$ receptor, which causes alteration in chloride conductance and membrane polarization. In addition to being the site of neurotransmitter action, a number of drugs including the anxiolytic and sedating benzodiazepines bind lo this receptor. The $GABA_A$ receptor comprises a chloride channel that generally, but not invariably, opens in response to GABA, allowing chloride to enter the cell. This, in turn, effects a slowing of neuronal activity through hyperpolarization of the cell membrane potential.

$GABA_A$ receptors are composed of five protein subunits. A number of cDNAs for these $GABA_A$ receptor subunits have been cloned and their primary structures determined. While these subunits share a basic motif of 4 membrane-spanning helices, there is sufficient sequence diversity to classify them into several groups. To date at least 6α, 3β, 3γ, 1ε, 1δ and 2ρ subunits have been identified. Native $GABA_A$ receptors are typically composed of 2α, 2β, and 1γ. Various lines of evidence (such as message distribution, genome localization and biochemical study results) suggest that the major naturally occurring receptor combinations are $α_1β_2γ_2$, $α_2β_3γ_2$, $α_3β_3γ_2$, and $α_5β_3γ_2$ (Mohler et al., *Neuroch. Res.* 1995; 20(5):631–36).

The $GABA_A$ receptor binding sites for GABA (2 per receptor complex) are formed by amino acids from the α and β subunits. Amino acids from the α and γ subunits together form one benzodiazepine site per receptor. Benzodiazepines exert their pharmacological actions by interacting with the benzodiazepine binding sites associated with the $GABA_A$ receptor. In addition to the benzodiazepine site (sometimes referred to as the benzodiazepine or BDZ receptor), the $GABA_A$ receptor contains sites of interaction for several other classes of drugs. These include a steroid binding site, a picrotoxin site, and a barbiturate site. The benzodiazepine site of the $GABA_A$ receptor is a distinct site on the receptor complex that does not overlap with the site of interaction for other classes of drugs that bind to the receptor or for GABA (see, e.g., Cooper, et at., The Biochemical Basis of Neuropharmacology, 6$^{th}$ ed., 1991, pp. 145–148, Oxford University Press, New York).

In a classic allosteric mechanism, the binding of a drug to the benzodiazepine site increases the affinity of the GABA receptor for GABA. Benzodiazepines and related drugs that enhance the ability of GABA to open $GABA_A$ receptor channels are known as agonists or partial agonists depending on the level of GABA enhancement. Other classes of drugs, such as β-carboline derivatives, that occupy the same site and negatively modulate the action of GABA are called inverse agonists. A third class of compounds exists which occupy the same site as both the agonists and inverse agonists and yet have little or no effect on GABA activity. These compounds will, however, block the action of agonists or inverse agonists and are thus referred to as $GABA_A$ receptor antagonists.

The important allosteric modulatory effects of drugs acting at the benzodiazepine site were recognized early, and the distribution of activities at different subtype receptors has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have enjoyed long pharmaceutical use as anxiolytics, these compounds are known to exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when used in combination with $GABA_A$ selective ligands than when used alone.

DESCRIPTION OF THE RELATED ART

Cyclohexanone pyrrole carboxamide compounds of the following general Formula A have been previously disclosed as modulators of $GABA_A$ receptors.

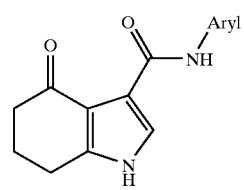

Formula A

PCT publications WO 95/11885, WO 97/26243, WO 9734870, WO 98/02420, and WO 00/23862 U.S. Pat. Nos. 5,484,944, 5,608,079, 5,750,702, 5,925,770, 5,637,724, 5,804,686, 5,849,927, 6,080,873, and 6,211,365, all of which are assigned to Neurogen Corporation, disclose structures of Formula A.

SUMMARY OF THE INVENTION

This invention relates to certain novel cycloalkylpyrrole-3-carboxylic acid derivatives and heterocycloalkylpyrrole-3-carboxylic acid derivatives that bind with high affinity and high selectivity to the benzodiazepine site of $GABA_A$ receptors, including human $GABA_A$ receptors. Compounds of the invention bind with high selectivity and/or high affinity to $GABA_A$ receptors and thereby act as agonists, antagonists or inverse agonists of such receptors. As such, they are useful in the treatment of various CNS disorders.

The invention provides novel compounds of Formula I (shown below), and pharmaceutical compositions comprising compounds of Formula I.

The invention further comprises methods of treating patients suffering from certain CNS disorders with an effective amount of a compound of the invention. The patient may be a human or other mammal. Treatment of humans, domesticated companion animals (pets) or livestock animals suffering from certain CNS disorders with an effective amount of a compound of the invention is encompassed by the invention.

In a separate aspect, the invention provides a method of potentiating the actions of other CNS active compounds. This method comprises administering an effective amount of a compound of the invention in conjunction with the administration of another CNS active compound.

Additionally this invention relates to the use of compounds of Formula I as probes for the localization of $GABA_A$ receptors in tissue sections.

Accordingly, in a broad aspect the invention is directed to compounds of Formula I,

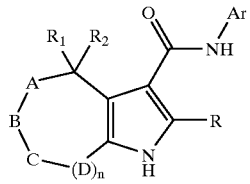

Formula I and the pharmaceutically acceptable salts thereof, wherein:

R is selected from halogen, cyano, nitro, and amino;

$R_1$ is chosen from amino, fluoro, hydroxy, $C_1$–$C_6$ alkoxy, arylamino, heteroarylamino, aryloxy, or heteroaryloxy; and $R_2$ is chosen from hydrogen, fluoro, $C_1$–$C_6$ alkyl, and aryl($C_1$–$C_4$alkyl); or $R_1$ and $R_2$ together represent an oxo group; or $R_1$ and $R_2$ are joined to form a saturated, or partially unsaturated ring of from 4 to 8 members containing 1 or more heteroatoms, preferably from 1 to 4 heteroatoms, independently chosen from N, S, and O, with the proviso that no two heteroatoms, with the exception of amino groups (forming a hydrazino group) are adjacent to each other;

n is 0, 1, or 2;

A is chosen from O, $NR_3$, and $CR_{3'}R_{3''}$;

B is chosen from O, $NR_4$, and $CR_{4'}R_{4''}$;

C is chosen from O, $NR_5$, and $CR_{5'}R_{5''}$;

each D is independently selected from O, $NR_6$, and $CR_{6'}R_{6''}$;

each $R_3$, $R_4$, $R_5$, and $R_6$ is independently selected from hydrogen, $C_1$–$C_6$ alkyl$_1$, $C_2$–$C_6$alkenyl$_1$, $C_2$–$C_6$alkynyl$_1$, $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$), hydroxy($C_1$–$C_6$ alkyl$_1$), amino($C_2C_6$ alkyl$_1$), aryl$_1$, aryl$_1$($C_1$–$C_4$alkyl$_1$), heteroaryl$_1$, and heteroaryl$_1$($C_1$–$C_4$alkyl$_1$);

each $R_{3'}$, $R_{3''}$, $R_{4'}$, $R_{4''}$, $R_{5'}$, $R_{5''}$, $R_{6'}$, and $R_{6''}$ is independently selected from hydrogen, halogen, hydroxy, amino, cyano, nitro, oxo, $C_1$–$C_6$ alkyl$_1$, $C_1$–$C_6$ alkoxy$_1$, $C_2$–$C_6$alkenyl$_1$, $C_2$–$C_6$alkynyl$_1$, $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$), halo($C_1$–$C_6$)alkyl$_1$, halo($C_1$–$C_6$)alkoxy$_1$ hydroxy($C_1$–$C_6$ alkyl$_1$), amino($C_1$–$C_6$ alkyl$_1$), mono or di($C_1$–$C_6$alkyl$_1$)amino, mono- or di($C_1$–$C_6$alkyl$_1$)amino($C_1$–$C_6$alkyl$_1$), aryl$_1$, aryl$_1$($C_1$–$C_4$alkyl$_1$), heteroaryl$_1$, and heteroaryl$_1$($C_1$–$C_4$alkyl$_1$);

wherein each alkyl$_1$, alkenyl$_1$, alkynyl$_1$, alkoxyl, cycloalkyl$_1$, heterocycloalkyl$_1$, aryl$_1$, and heteroaryl$_1$ is unsubstituted or substituted with one or more substituents selected from: hydroxy, oxo, halogen, amino, cyano, nitro, $C_1$–$C_6$alkyl, $C_1$–$C_6$alkoxy, and mono- or di-($C_1$–$C_6$alkyl)amino;

with the proviso that:

a) at least one of B, C, and D is nitrogen and is substituted by $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$), hydroxy($C_1$–$C_6$ alkyl$_1$), amino($C_1$–$C_6$ alkyl$_1$), aryl$_1$, aryl$_1$($C_1$–$C_4$alkyl$_1$), heteroaryl$_1$, and heteroaryl$_1$($C_1$–$C_4$alkyl$_1$); or b) at least one of B, C, and D are carbon and is substituted by halogen, hydroxy, amino, cyano, nitro, oxo, $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$), halo($C_1$–$C_6$)alkyl$_1$, halo($C_1$–$C_6$)alkoxyl$_1$, hydroxy ($C_1$–$C_6$ alkyl$_1$), amino($C_1$–$C_6$ alkyl$_1$), mono- or di(($C_1$–$C_6$alkyl$_1$)amino, mono- or di(($C_1$–$C_6$alkyl$_1$) amino($C_1$–$C_6$alkyl$_1$), aryl$_1$, aryl$_1$($C_1$–$C_4$alkyl$_1$), heteroaryl$_1$, and heteroaryl$_1$($C_1$–$C_4$alkyl$_1$); or c) A is carbon and is substituted by halogen, hydroxy, amino, cyano, nitro, oxo, $C_1$–$C_6$alkoxy, halo($C_1$–$C_6$) alkyl$_1$, halo($C_1$–$C_6$)alkoxy$_1$, hydroxy($C_1$–$C_6$ alkyl$_1$), or d) n is 1 or 2 and at least one of B, C, or D is nitrogen or oxygen; or e) any of $R_{3'}$ and $R_{3''}$, $R_{4'}$ and $R_{4''}$, $R_{5'}$ and $R_{5''}$, and $R_{6'}$, and $R_6$ may be joined to form a saturated, partially unsaturated, or unsaturated carbocyclic or heterocyclic ring of from a 4–8 membered ring$_1$;

wherein said ring$_1$ is a saturated, partially unsaturated, or unsaturated carbocyclic or heterocyclic ring of from 3–8 ring members which contains 0, 1, or 2 heteroatoms independently chosen from O, N, and S, and said ring, is unsubstituted or is substituted by 1, 2, or 3 substituents independently chosen from halogen, hydroxy, amino, cyano, nitro, oxo, $C_1$–$C_6$ alkyl, $C_1$–$C_6$ alkoxy, $C_2$–$C_6$alkenyl, $C_2$–$C_6$alkynyl, halo($C_1$–$C_6$) alkyl, halo($C_1$–$C_6$)alkoxy hydroxy($C_1$–$C_6$ alkyl), amino($C_1$–$C_6$ alkyl), mono- or di($C_1$–$C_6$alkyl)amino, and mono- or di($C_1$–$C_6$alkyl)amino($C_1$–$C_6$alkyl);

Ar is a group of the formula

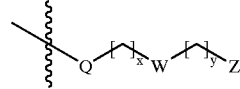

Q is an optionally substituted carbocyclic aryl or optionally substituted heteroaryl group having from 1 to 3 rings, 5 to 6 members in each ring and from 1 to 3 heteroatoms;

W is hydrogen, oxygen, nitrogen, sulfur, or $CR^7R^8$ where $R^7$ and $R^8$ are the same or different and represent hydrogen, $C_1$–$C_6$ alkyl, or $R^7$ and $R^8$ may be taken together to represent a cyclic moiety having 3–7 carbon atoms;

Z is hydrogen, hydroxy, $C_1$–$C_6$ alkoxy, $C_3$–$C_7$ cycloalkyl, $C_3$–$C_7$ cycloalkyl($C_1$–$C_4$alkoxy), amino, mono or di($C_1$–$C_6$alkyl)amino, or $NR^9COR^{10}$ where $R^9$ and $R^{10}$ are the same or different and represent hydrogen or $C_1$–$C_6$ alkyl, or $R^9$ and $R^{10}$ may be joined to from a $C_3$–$C_7$ cycloalkyl ring, or Z is optionally substituted carbocyclic aryl or optionally substituted heteroaryl group having from 1 to 3 rings, 5 to 6 members in each ring and from 1 to 3 heteroatoms;

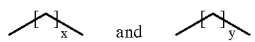

represent carbon chains which are independently substituted or substituted with halogen, cyano, nitro, amino, mono or di($C_1$–$C_6$alkyl)amino, $C_2$–$C_6$alkenyl, $C_2$–$C_6$alkynyl, $C_1$–$C_6$alkoxy, trihalomethyl, trihalomethoxy, $C_1$–$C_6$alkyl, or $C_3$–$C_7$ cycloalkyl, x is 0, 1, 2, or 3; and y is 0, 1, 2, or 3.

The novel compounds encompassed by the invention are described by the general Formula I (set forth above) and the pharmaceutically acceptable non-toxic salts thereof.

The invention further encompasses compounds of Formula I, above, in which

R, $R_1$, $R_2$, A, B, C, D, and n are as defined above and

Q is chosen from phenyl, naphthyl, quinolinyl, thienyl, pyridyl, pyrimidinyl, pyrazinyl, oxazolyl, isoxazolyl, symmetrical or unsymmetrical oxadiazolyl, symmetrical or unsymmetrical thiadiazolyl, symmetrical or unsymmetrical triazolyl, pyrazolyl, furanyl, diazenyl, triazenyl, or triazolopyrazinyl group;

each of which is unsubstituted or substituted with up to three substituents independently selected from i) and ii) wherein i) is hydroxy, cyano, halogen, nitro, amino, mono or di($C_1$–$C_6$)alkylamino, $C_2$–$C_6$alkenyl, $C_2$–$C_6$alkynyl, $C_1$–$C_6$alkoxy, trihalomethyl, and trihalomethoxy;

ii) is $C_1$–$C_6$alkyl optionally containing heteroatoms and optionally substituted with one or more carbocyclic or heterocyclic group;

W is hydrogen, oxygen, nitrogen, sulfur, or $CR^7R^8$ where $R^7$ and $R^8$ are the same or different and represent hydrogen, $C_1$–$C_6$alkyl, or $R^7$ and $R^8$ may be taken together to represent a cyclic moiety having 3–7 carbon atoms;

Z is hydrogen, hydroxy, $C_1$–$C_6$alkoxy, $C_3$–$C_7$cycloalkyl, $C_3$–$C_7$cycloalkyl($C_{1-3}$alkoxy), amino, mono or di($C_1$–$C_6$alkyl)amino, a carbocyclic or haterocylic group, or $NR^9COR^{10}$ where $R^9$ and $R^{10}$ are the same or different and represent hydrogen or $C_1$–$C_6$alkyl, or $R^9$ and $R^{10}$ may be joined to from a $C_3$–$C_7$ cycloalkyl ring, or Z is a phenyl, napthyl, quinolinyl, thienyl, thiazolyl, pyridyl, pyrimidinyl, imidazolyl, pyrazolyl, pyrazinyl, pyridizinyl, piperidinyl, oxazolyl, isoxazolyl, symmetrical or unsymmetrical thiadiazolyl, symmetrical or unsymmetrical triazofyl, symmetrical or unsymmetrical oxadiazolyl, pyrrolyl, furanyl, pyrimidinyl, diazenyl, triazenyl, 1, 2, 4-triazolone, 4,5-dihydroimidazolyl, or a 1,4,5,6-tetrahydropyrimidinyl group;

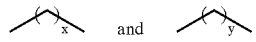

represent carbon chains which are unsubstituted or substituted with up to three groups independently chosen from halogen, cyano, nitro, amino, mono- or di($C_1$–$C_6$alkyl)amino, $C_2$–$C_6$alkenyl, $C_2$–$C_6$alkynyl, $C_1$–$C_6$alkoxy, trihalomethyl, trihalomethoxy, straight or branched chain $C_1$–$C_6$alkyl, or $C_3$–$C_7$cycloalkyl, and m is 0, 1, 2, or 3; and n is 0, 1, 2, or 3.

Such compounds will be referred to as compounds of Formula Ia.

Also particularly provided by the invention are compounds of Formula II:

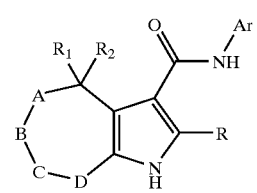

Formula II i.e. compounds in which n, shown in Formula 1, is 1 and R, $R_1$, $R_2$, A, B, C, D, and Ar are as defined either for Formula I or more preferably as defined for Formula Ia.

Further provided by the invention are compounds of Formula III:

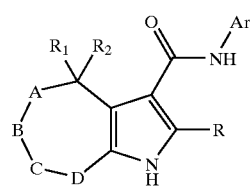

Formula III wherein R, Ar, and A, B, C, and D are as defined either for Formula I or more preferably as defined for Formula Ia.

Particularly embodied by the invention are compounds of Formula III in which

A is chosen from $NR_3$ and $CR_{3'}R_{3''}$;

B is chosen from $NR_4$ and $CR_{4'}R_{4''}$;

C is chosen from $NR_5$ and $CR_{5'}R_{5''}$;

D is chosen from $NR_6$ and $CR_{6'}R_{6''}$; and not more than 2 members of the ring containing A, B, C, and D are nitrogen.

Another embodiment of the invention includes compounds of Formula IV

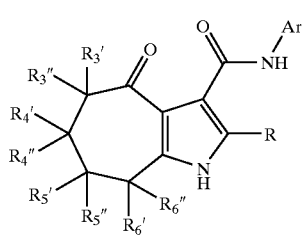

Formula IV wherein R, Ar, $R_3$, $R_{3'}$, $R_{3''}$, $R_4$, $R_{4'}$, $R_{4''}$, $R_5$, $R_{5'}$, $R_{5''}$, $R_6$, $R_{6'}$ and $R_{6''}$ are as are as defined either for Formula I or more preferably as defined for Formula Ia.

Particular embodiments of the invention include compounds of Formula IV in which Ar is phenyl, pyridyl or pyrimidinyl,
  each of which is unsubstituted or substituted with up to three substituents independently selected from hydroxy, cyano, halogen, nitro, amino, mono or di($C_1$–$C_6$)alkylamino, $C_2$–$C_6$alkenyl, $C_2$–$C_6$alkynyl, $C_1$–$C_6$alkyl, $C_1$–$C_6$alkoxy, trihalomethyl, or trihalomethoxy.

Another specific embodiment of the invention includes compounds of Formula V

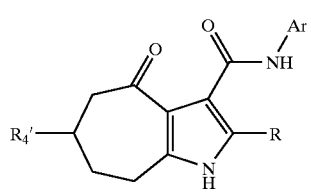

Formula V wherein R is are as defined either for Formula I or more preferably as defined for Formula Ia;

Ar is chosen from phenyl, pyridyl and pyrimidinyl,
  each of which is unsubstituted or substituted with up to three substituents independently selected from hydroxy, cyano, halogen, nitro, amino, mono or di($C_1$–$C_6$)alkylamino, $C_2$–$C_6$alkenyl, $C_2$–$C_6$alkynyl, $C_1$–$C_6$alkyl, $C_1$–$C_6$alkoxy, trihalomethyl, or trihalomethoxy; and $R_4'$ is chosen from $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$), aryl$_1$, aryl$_1$($C_1$–$C_4$alkyl$_1$), heteroaryl$_1$, and heteroaryl$_1$($C_1$–$C_4$alkyl$_1$);

wherein each alkyl$_1$, cycloalkyl$_1$, heterocycloalkyl$_1$, aryl$_1$, and heteroaryl$_1$ is unsubstituted or substituted with one or more substituents selected from: hydroxy, oxo, halogen, amino, cyano, nitro, $C_1$–$C_6$alkyl, $C_1$–$C_6$alkoxy, amino($C_1$–$C_6$alkyl); mono- or di-($C_1$–$C_6$alkyl)amino, and mono- or di-($C_1$–$C_6$alkyl)amino($C_1$–$C_6$alkyl).

Also included in the invention are compounds and salts of Formula VI

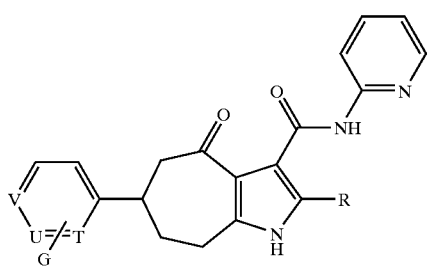

Formula VI wherein
  R is selected from hydrogen, halogen, methyl, and ethyl; V, U, and T, independently represent N or CH; and G represents up to 3 groups independently chosen from hydrogen, hydroxy, oxo, halogen, amino, cyano, nitro, $C_1$–$C_6$alkyl, $C_1$–$C_6$alkoxy, and mono or di- amino ($C_1$–$C_6$alkyl).

Another preferred embodiment of the invention includes compounds of Formula I, as set forth above, wherein R, $R_1$, $R_2$, Ar, A, B,C, D, n and Ar are as defined for Formula I:
  with the proviso that either $R_3$ or $R_3'$ and $R_4$ or $R_4'$ form an unsaturated, partially saturated, or saturated ring of from 5 to 7 members or $R_4$ or $R_4'$ and $R_5$ or $R_5'$ form an unsaturated, partially saturated, or saturated ring of from 5 to 7 members, wherein said unsaturated, partially saturated, or saturated ring contains 0, 1, or 2 heteroatoms independently chosen from S, O, or N and said unsaturated, partially saturated, or saturated ring is unsubstituted or substituted with up to 3 substitutents independently chosen from:

halogen, hydroxy, amino, cyano, nitro, oxo, $C_1$–$C_6$alkyl, $C_1$–$C_6$alkoxy, $C_2$–$C_6$alkenyl, $C_2$–$C_6$alkynyl, $C_3$–$C_7$cycloalkyl$_2$, $C_3$–$C_7$cycloalkyl$_2$($C_1$–$C_4$alkyl), heterocycloalkyl$_2$, heterocycloalkyl$_2$($C_1$–$C_4$alkyl), halo($C_1$–$C_6$)alkyl, halo($C_1$–$C_6$)alkoxy, hydroxy($C_1$–$C_6$ alkyl), amino($C_1$–$C_6$ alkyl$_2$, mono- or di($C_1$–$C_6$alkyl$_2$) amino, aryl$_2$, aryl$_2$($C_1$–$C_4$alkyl), heteroaryl$_2$, and heteroaryl$_2$($C_1$–$C_4$alkyl);

wherein each cycloalkyl$_2$, heterocycloalkyl$_2$, aryl$_2$, and heteroaryl$_2$ is unsubstituted or substituted with one or more substituents selected from: hydroxy, oxo, halogen, amino, cyano, nitro, $C_1$–$C_6$alkyl, $C_1$–$C_6$alkoxy, and mono- or di-amino($C_1$–$C_6$alkyl).

Such compounds will be referred to as compounds of Formula VII.

Particularly preferred compounds of this class are those compounds wherein n is 1 or 2, but preferably 1, and the variables Q, W, and Z, which are part of the group Ar are defined as follows:

Q is a phenyl, naphthyl, quinolinyl, thienyl, pyridyl, pyrimidinyl, pyrazinyl, oxazolyl, isoxazolyl, symmetrical or unsymmetrical oxadiazolyl, symmetrical or unsymmetrical thiadiazolyl, symmetrical or unsymmetrical triazolyl, pyrazolyl, furanyl, diazenyl, triazenyl, or triazolopyrazinyl group;

each of which is unsubstituted or substituted with up to three substituents independently selected from i) and ii) wherein i) represents hydroxy, cyano, halogen, nitro, amino, mono or di(($C_1$–$C_6$)alkylamino, $C_2$–$C_6$alkenyl, $C_2$–$C_6$alkynyl, $C_1$–$C_6$alkoxy, trihalomethyl, or trihalomethoxy;

ii) represents $C_1-C_6$alkyl optionally containing heteroatoms and optionally substituted with one or more carbocyclic or heterocyclic group;

W is hydrogen, oxygen, nitrogen, sulfur, or $CR^7R^8$ where $R^7$ and $R^8$ are the same or different and represent hydrogen, $C_1-C_6$alkyl, or $R^7$ and $R^8$ may be taken together to represent a cyclic moiety having 3–7 carbon atoms;

Z is hydrogen, hydroxy, $C_1-C_6$alkoxy, $C_3-C_7$cycloalkyl, $C_3-C_7$ cycloalkyl($C_{1-3}$alkoxy), amino, mono or di($C_1-C_6$alkyl)amino, a carbocyclic or heterocylic group, or $NR^9COR^{10}$ where $R^9$ and $R^{10}$ are the same or different and represent hydrogen or $C_1-C_6$alkyl, or $R^9$ and $R^{10}$ may be joined to from a $C_3-C_7$ cycloalkyl ring, or Z is a phenyl, napthyl, quinolinyl, thienyl, thiazolyl, pyridyl, pyrimidinyl, imidazolyl, pyrazolyl, pyrazinyl, pyridizinyl, piperidinyl, oxazolyl, isoxazolyl, symmetrical or unsymmetrical thiadiazolyl, symmetrical or unsymmetrical triazolyl, symmetrical or unsymmetrical oxadiazolyl, pyrrolyl, furanyl, pyrimidinyl, diazenyl, triazenyl, 1, 2, 4-triazolone, 4,5-dihydroimidazolyl, or a 1,4,5,6-tetrahydropyrimidinyl group;

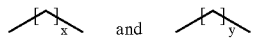

represent carbon chains which is unsubstituted or substituted with up to three groups independently chosen from halogen, cyano, nitro, amino, mono- or di($C_1-C_6$alkyl)amino, $C_2-C_6$alkenyl, $C_2-C_6$alkynyl, $C_1-C_6$alkoxy, trihalomethyl, trihalomethoxy, straight or branched chain $C_1-C_6$alkyl, or $C_3-C_7$cycloalkyl, and x is 0, 1, 2, or 3; and y is 0, 1, 2, or 3.

Such compounds will be referred to a compounds of Formula VIIa. Preferred compounds of Formula VIIa are those compounds wherein n is 1 and $R_1$ and $R_2$ form an oxo group. Other preferred compounds of Formula VIIa are those compounds in which n is 1, $R_1$ and $R_2$ form an oxo group, A is chosen from $NR_3$ and $CR_3R_{3''}$; B is chosen from $NR_4$ and $CR_4R_{4''}$, C is chosen from $NR_5$ and $CR_{5'}R_{5''}$, D is chosen from $NR_6$ and $CR_{6'}R_{6''}$, and not more than 2 members of the ring containing A, B, C, and D are nitrogen. Still other specific embodiments of the invention include compounds in which n is 1, $R_1$ and $R_2$ form an oxo group, and A is $CR_3R_{3''}$; B is $CR_4R_{4''}$; C is $CR_{5'}R_{5''}$; and D is $CR_{6'}R_{6''}$. Also included in the invention are compounds of Formula VIIa wherein n is 1, $R_1$ and $R_2$ form an oxo group, and A is $CR_3R_{3''}$; B is $CR_4R_{4''}$; C is $CR_{5'}R_{5''}$; and D is $CR_{6'}R_{6''}$, Ar is phenyl, pyridyl or pyrimidinyl, each of which may be unsubstituted or substituted with up to three substituents independently selected from hydroxy, cyano, halogen, nitro, amino, mono or di($C_1-C_6$)alkylamino, $C_2-C_6$alkenyl, $C_2-C_6$alkynyl, $C_1-C_6$alkyl, $C_1-C_6$alkoxy, trihalomethyl, or trihalomethoxy.

Also included in the invention are compounds and salts of Formula VIII

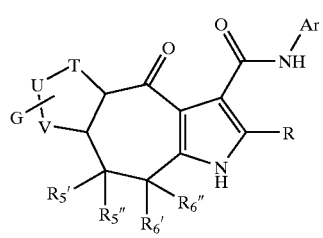

Formula VIII wherein:

R is as defined in as for Specific Embodiment VIIa $R_{5'}$, $R_{5''}$, $R_{6'}$, and $R_{6''}$ are independently chosen at each occurrence from hydrogen, halogen, hydroxy, amino, cyano, nitro, oxo, $C_1-C_6$ alkyl, $C_1-C_6$ alkoxy, $C_2-C_6$alkenyl, $C_2-C_6$alkynyl, halo($C_1-C_6$)alkyl, halo($C_1-C_6$)alkoxy, hydroxy($C_1-C_6$ alkyl), amino($C_1-C_6$ alkyl), mono- or di($C_1-C_6$alkyl)amino;

T, U, and V are independently chosen from O, S, $CH_2$, and NH;

G represents 0 to 3 substituents independently chosen from halogen, hydroxy, amino, cyano, nitro, oxo, $C_1-C_6$alkyl, $C_1-C_6$alkoxy, $C_2-C_6$alkenyl, $C_2-C_6$alkynyl, $C_3-C_7$cycloalkyl$_2$, $C_3-C_7$cycloalkyl$_2$($C_1-C_4$alkyl), heterocycloalkyl$_2$, heterocycloalkyl$_2$($C_1-C_4$alkyl), halo($C_1-C_6$)alkyl, halo($C_1-C_6$)alkoxy, hydroxy($C_1-C_6$ alkyl), amino($C_1-C_6$ alkyl$_2$, mono- or di($C_1-C_6$alkyl$_2$)amino, aryl$_2$, aryl$_2$($C_1-C_4$alkyl), heteroaryl$_2$, and heteroaryl2($C_1-C_4$alkyl);

wherein each cycloalkyl$_2$, heterocycloalkyl$_2$, aryl$_2$, and heteroaryl$_2$ is unsubstituted or substituted with one or more substituents selected from: hydroxy, oxo, halogen, amino, cyano, nitro, $C_1-C_6$alkyl, $C_1-C_6$alkoxy, and mono- or di-amino($C_1-C_6$alkyl); and Ar is phenyl, pyridyl or pyrimidinyl, each of which is unsubstituted or substituted with up to three substituents independently selected from hydroxy, cyano, halogen, nitro, amino, mono or di($C_1-C_6$)alkylamino, $C_2-C_6$alkenyl, $C_2-C_6$alkynyl, $C_1-C_6$alkyl, $C_1-C_6$alkoxy, trihalomethyl, or trihalomethoxy.

Preferred compounds and salts of Formula VIII are those compounds in which $R_{5'}$, $R_{5''}$, $R_{6'}$, and $R_{6''}$ are all hydrogen, Ar is as defined for compounds of Formula VIIa; R is chosen from hydrogen, halogen, methyl, and ethyl;

T', U', and V' are independently chosen from O, S, $CH_2$, and NH; and

G' represents up to 3 substituents independently chosen from halogen, hydroxy, amino, cyano, nitro, oxo, $C_1-C_6$alkyl, $C_1-C_6$alkoxy, $C_2-C_6$alkenyl, $C_2-C_6$alkynyl, $C_3-C_7$cycloalkyl$_2$, $C_3-C_7$cycloalkyl$_2$($C_1-C_4$alkyl), heterocycloalkyl$_2$, heterocycloalkyl$_2$($C_1-C_4$alkyl), halo($C_1-C_6$)alkyl, halo($C_1-C_6$)alkoxy, hydroxy($C_1-C_6$ alkyl), amino($C_1-C_6$ alkyl$_2$, mono- or di($C_1-C_6$alkyl$_2$)amino, aryl$_2$, aryl$_2$($C_1-C_4$alkyl), heteroaryl$_2$, and heteroaryl$_2$($C_1-C_4$alkyl);

wherein each cycloalkyl$_2$, heterocycloalkyl$_2$, aryl$_2$, and heteroaryl$_2$ is unsubstituted or substituted with one or more substituents selected from: hydroxy, oxo, halogen, amino, cyano, nitro, $C_1-C_6$alkyl, $C_1-C_6$alkoxy, and mono- or di-amino($C_1-C_6$alkyl).

Another embodiment of the invention is directed to compounds and salts of Formula IX

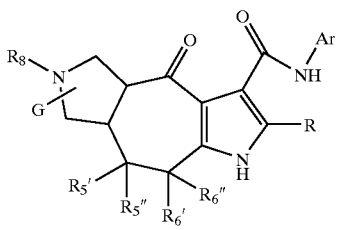

Formula IX wherein Ar is as defined for compounds of Formula VIIa;
R is chosen from hydrogen, halogen, methyl, and ethyl;
$R_{5'}$, $R_{5''}$, $R_{6'}$, and $R_{6''}$ are independently chosen at each occurrence from hydrogen, halogen, hydroxy, amino, $C_1$–$C_6$ alkyl, $C_1$–$C_6$ alkoxy, trihalomethyl, and trifluoromethoxy; and G represents 0 to 3 substituents independently chosen from halogen, hydroxy, amino, cyano, nitro, oxo, $C_1$–$C_6$ alkyl, $C_1$–$C_6$ alkoxy, $C_2$–$C_6$ alkenyl, $C_2$–$C_6$ alkynyl, $C_3$–$C_7$ cycloalkyl$_2$, $C_3$–$C_7$ cycloalkyl$_2$ ($C_1$–$C_4$ alkyl), heterocycloalkyl$_2$, heterocycloalkyl$_2$ ($C_1$–$C_4$ alkyl), halo($C_1$–$C_6$)alkyl, halo($C_1$–$C_6$)alkoxy, hydroxy($C_1$–$C_6$ alkyl), amino($C_1$–$C_6$ alkyl$_2$, mono- or di($C_1$–$C_6$ alkyl$_2$)amino, aryl$_2$, aryl$_2$($C_1$–$C_4$ alkyl), heteroaryl$_2$, and heteroaryl$_2$($C_1$–$C_4$ alkyl);

wherein each cycloalkyl$_2$, heterocycloalkyl$_2$, aryl$_2$, and heteroaryl$_2$ is unsubstituted or substituted with one or more substituents selected from: hydroxy, oxo, halogen, amino, cyano, nitro, $C_1$–$C_6$ alkyl, $C_1$–$C_6$ alkoxy, and mono- or di-amino($C_1$–$C_6$ alkyl); and $R_8$ is chosen from hydrogen and $C_1$–$C_6$ alkyl. Preferred compounds of Formula IX are those compounds in which Ar represents phenyl, pyridyl, or pyrimidinyl each or which may be unsubstituted or substituted with 1, 2, or 3, substituents chosen from hydroxy, halogen, amino, nitro, cyano, $C_1$–$C_6$ alkyl, $C_1$–$C_6$ alkoxy, trihalomethyl, trihalomethoxy, amino($C_1$–$C_6$ alkyl), mono- or di($C_1$–$C_6$ alkyl)amino, and mono- or di($C_1$–$C_6$ alkyl)amino($C_1$–$C_6$ alkyl).

Representative compounds of the present invention, which are encompassed by Formula I, include, but are not limited to the compounds set forth in Examples 1 to 8 and their pharmaceutically acceptable acid and base addition salts. If the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-ACOOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies that may be employed to prepare non-toxic pharmaceutically acceptable addition salts and acylated prodrugs of the compounds encompassed by Formula I. The invention further encompasses all enantiomers and diastereomers of the disclosed compounds. Those of ordinary skill in the art will readily recognize methods by which mixtures of enantiomers and diasteromers may be resolved. The definition of Formula I as used in herein include possible isomers, such as tautomers and rotamers.

This invention relates to novel cycloalkylpyrrole-3-carboxylic acid derivatives and heterocycloalkylpyrrole-3-carboxylic acid derivatives preferred examples of which bind with high affinity to the benzodiazepine site of GABA$_A$ receptors, including human GABA$_A$ receptors. Preferred cycloalkylpyrrole-3-carboxylic acid derivatives and heterocycloalkylpyrrole-3-carboxylic acid derivatives, that bind with high selectivity to the benzodiazepine site of GABA$_A$ receptors, including human GABA$_A$ receptors, are also included in this invention. Without wishing to be bound to any particular theory, it is believed that the interaction of the compounds of Formula I with the benzodiazepine site results in the pharmaceutical utility of these compounds.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treaung anxiety disorders such as panic disorder, obsessive compulsive disorder and generalized anxiety disorder, stress disorders including post-traumatic stress, and acute stress disorders. Compounds of the inventions that act as agonists at $\alpha_2\beta_3\gamma_2$ and $\alpha_3\beta_3\beta_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury. AIDS associated dementia, and dementia associated with depression, anxiety or psychosis.

Attention Deficit Disorder, e.g. attention deficit disorder (ADD), and attention deficit and hyperactivity disorder (ADHD).

Speech disorders, e.g. stuttering, including motor tic, clonic stuttering, dysfluency, speech blockage, dysarthria, Tourete syndrome or logospasm.

The invention also provides pharmaceutical compositions comprising one or more compounds of the invention together with a pharmaceutically acceptable carrier or excipient, for treating disorders responsive to $GABA_A$ receptor modulation, e.g., treatment of anxiety, depression, sleep disorders or cognitive impairment by $GABA_A$ receptor modulation. Pharmaceutical compositions include packaged pharmaceutical compositions comprising a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5-HT_{1A}$) agonists and antagonists; for anxiety and depression, neurokinin receptor antagonists or corticotropin releasing factor receptor ($CRF_1$) antagonists; for steep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)6-(1-methyl-1,2,3-triazol4-yl) methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The present invention also pertains to methods of inhibiting the binding of benzodiazepine compounds, such as Ro15-1788, or GABA to the $GABA_A$ receptors which methods involve contacting a solution containing compound of the invention with cells expressing $GABA_A$ receptors, wherein the compound is present at a concentration sufficient to inhibit benzodiazepine binding or GABA binding to $GABA_A$ receptors in vitro. This method includes inhibiting the binding of benzodiazepine compounds to $GABA_A$ receptors in vivo, e.g., in a patient given an amount of a compound of Formula I that would be sufficient to inhibit the binding of benzodiazepine compounds or GABA to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via a $GABA_A$ receptor binding assay, such as the assay described in Example 13. The $GABA_A$ receptors used to determine in vitro binding may be obtained from a variety of sources, for example from preparations of rat cortex or from cells expressing cloned human $GABA_A$ receptors.

The present invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 14. The cells expressing the GABA receptors in vivo may be, but are not limited to, neuronal cells or brain cells. Such cells may be contacted with compounds of the invention through contact with a body fluid containing the compound, for example through contact with cerebrospinal fluid. Alteration of the signal-transducing activity of $GABA_A$ receptors in vitro may be determined from a detectable change in the electrophysiology of cells expressing $GABA_A$ receptors, when such cells are contacted with a compound of the invention in the presence of GABA.

Intracellular recording or patch-clamp recording may be used to quantitate changes in electrophysiology of cells. A reproducible change in behavior of an animal given a compound of the invention may also be used to indicate that changes in the electrophysiology of the animal's cells expressing $GABA_A$ receptors has occurred.

The $GABA_A$ receptor ligands provided by this invention and labeled derivatives hereof are also useful as standards and reagents in determining the ability of a potential pharmaceutical to bind to the $GABA_A$ receptor. Radiolabeled derivatives the $GABA_A$ receptor ligands provided by this invention are also useful as radiotracers for positron emission tomography (PET) imaging or for single photon emission computerized tomography (SPECT).

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

When any variable occurs more than one time in any constituent or formula for a compound, its definition at each occurrence is independent of its definition at every other occurrence. Thus, for example, if a group is shown to be substituted with 0 to 3 R*, (where R* indicates any variable group such as R, $R_1$, $R_3$, $R_3$* etc.) then said group may optionally be substituted with up to three R* groups and R* at each occurrence is selected independently from the definition of R*. Also, combinations of substituents and/or variables are permissible only if such combinations result in stable compounds.

As used herein, "alkyl" is intended to include both branched and straight-chain aliphatic hydrocarbon groups, having the specified number of carbon atoms. Alkyl groups of 2 or more carbon atoms may contain double or triple bonds. Examples of alkyl include, but are not limited to, methyl, ethyl, n-propyl, i-propyl, n-butyl, s-butyl, t-butyl, n-pentyl, and s-pentyl. Preferred alkyl groups are $C_1$–$C_6$ alkyl groups. "$C_1$–$C_6$ alkyl" indicates alkyl groups having from 1 to about 6 carbon atoms.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. "$C_1$–$C_6$ alkoxy" indicates alkoxy groups having from 1 to about 6 carbon atoms.

"Alkenyl" is intended to include hydrocarbon chains of either a straight or branched configuration comprising one or more unsaturated carbon-carbon bonds which may occur in any stable point along the chain, such as ethenyl and propenyl. Alkenyl groups typically will have 2 to about 12 carbon atoms, more typically 2 to about 8 carbon atoms.

"Alkynyl" is intended to include hydrocarbon chains of either a straight or branched configuration comprising one or more triple carbon-carbon bonds which may occur in any stable point along the chain, such as ethynyl and propynyl. Alkynyl groups typically will have 2 to about 12 carbon atoms, more typically 2 to about 8 carbon atoms.

"Aryl" is intended to include groups that, in accordance with the theory of Hückel, have a cyclic, delocalized (4n+2) pi-electron system. Examples of aryl groups include, but are not limited to, arenes and their substitution products, e.g. phenyl, naphthyl and toluyl, among numerous others.

"Carbocyclic Aryl" refers to optionally substituted aromatic groups having 1 or more rings, wherein the members of the aromatic ring or rings are carbon. Such groups include optionally substituted phenyl and optionally substituted naphthyl.

The term "heteroaryl" is intended to include aromatic heterocyclic groups and includes the non-limiting examples thiophenyl, pyridyl, pyrimidyl, pyridazyl, oxazolyl, isooxazolyl, thiazolyl and isothiazolyl, among others.

The term "Cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "(cycloalkyl)alkyl", Cycloalkyl and alkyl are as defined above and the point of attachment is on the alkyl group. This term encompasses, but is not limited to, cyclopropylmethyl, cyclohexylmethyl, cyclohexylmethyl.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, difluoromethyl, trichloromethyl, pentafluoroethyl, and pentachloroethyl.

As used herein, "haloalkoxy" indicates a haloalkyl group as defined above with the indicated number of carbon atoms attached through an oxygen bridge. Examples of haloalkoxy groups include, but are not limited to, trifluoromethoxy and trichloromethoxy.

As used herein, the terms "heterocyclic ring" and "heterocyclic group" are intended to mean a stable 5- to 7-membered monocyclic or bicyclic or 7- to 10-membered bicyclic heterocyclic ring which is saturated, partially unsaturated, or unsaturated ("heteroaryl"), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The term or "heterocycloalkyl" is used to refer to saturated heterocyclic groups.

The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heterocyclic groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl. Also included are fused ring and spiro compounds containing, for example, the above heterocycles.

The term "oxo" indicates a carbonyl group. When an oxo group appears as a substituent the allowed valence of the substituted position is not exceeded.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, $HOOC-(CH_2)n-COOH$ where n is 0–4, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985).

The terms "trihaloalkyl" and "trihaloalkoxy" refer to particular types of haloalkyl and haloalkoxy groups that contain three halogen atoms, e.g., trichloromethyl, trifluoromethyoxy.

The term "protecting group" is used to describe a group which is unreactive (inert) under certain reaction conditions which are used to produce final compounds according to the present invention or to intermediates which are used to synthesize compounds according to the present invention. Protecting groups according to the present invention may be readily removed under selective conditions (acid, base, fluoride anion, zinc, etc.) as is well-known in the art. This term is well-known in the art and is given its art recognized definition in describing the present invention and in particular, methods of synthesizing compounds according to the present invention.

The term "potentiate" is used to describe the pharmacological activity of compounds according to the present invention in increasing the activity of CNS agents which are co-administered with compounds according to the present invention. It is an unexpected result that compounds according to the present invention may be coadministered with other CNS agents and produce a combined effect which is more than additive (synergistic). Other CNS agents which may be administered in combination with compounds according to the present invention include the non-limiting examples, for anxiety, serotonin receptor (e.g., 5HT1A) agonists and antagonists; for anxiety and depression, neurokinin receptor antagonists or corticotropin releasing factor receptor (CRF1) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. In particular aspects, the present invention provides a method of potentiating the antidepressant activity of selective serotonin inhibitors (SSRIs) by administering an effective amount of a GABA agonist compound of the invention in combination with an SSRI.

Combination therapy or administration may be carried out analogously according to the method of any one or more of Da-Rocha, et al., *J. Psychopharmacology* (1997) 11 (3) 211–218; Smith, et al., *Am. J. Psychiatry* (1988) 155(10) 1339–45; or Le, et al., *Alcohol and Alcoholism* (1996) 31 Suppl. 127–132. Also see, the discussion of the use of the GABAA receptor ligand 3-(5-methylisoxazol-3-yl)-6-(1-methyl-1,2,3-triazol-4-yl)methyloxy-1,2,4-triazolo [3,4-a] phthalzine in combination with nicotinic agonists, muscarinic agonists, and acetylcholinesterase inhibitors, in international patent applications WO 99/47142, WO 99/47171 and WO 99/47131, respectively. Also, see in this regard international application No. WO 99/37303 for its discussion of the use of a class of GABAA receptor ligands, such as the 1,2,4-triazolo[4,3-b]pyridazines, in combination with SSRIs.

The term "effective" is used to describe amounts or concentrations of compounds according to the present invention which are used in pharmaceutical compositions and/or methods of treatment or use according to the present invention consistent with the intended use of the compound. An effective amount or concentration is that amount or concentation which produces an intended effect.

DETAILED DESCRIPTION OF THE INVENTION

An illustration of the preparation of compounds of the present invention is given in the following reaction schemes. The reactions shown below show specific methods for the synthesis of 3 types of compounds of the invention. However, one of ordinary skill in the art will recognize that reagents and reaction conditions may be varied to obtain specific end products. For example, a variety of methods for protecting amine groups, in addition to the BOC protection method shown, will be readily understood.

In general, synthesis of the compounds according to the present invention occur in a step-wise fashion in which the basic bicyclic structure (seven-membered ring fused to a substituted pyrrole, preferably an ester substituted pyrrole) is first substituted on the seven-membered ring where applicable (including creating a third ring structure) and the ester group (or other leaving group such as an active ester, tosyl, or halogen such as an acyl halide) on the pyrrole moiety of the molecule is then reacted with an appropriate amine (preferably, an aryl amine as defined or otherwise indicated herein) to produce the corresponding amide derivative (final compound). These compounds may be prepared in a number of ways using methods which are well-known in the art. By way of example, the final substituted bicyclic phenamide compounds of the schemes, may be prepared by the illustrated methods or by analogous methods readily available in the art.

By way of example, according to the method of Scheme I, the initial bicyclic ketone compound is N-Boc protected on the pyrrole group and subsequently phenylselenated at the position α to the ketone in the seven membered ring. Reaction of the phenylselenated derivative with hydrogen peroxide/pyridine in methylene chloride produces the eneone group in the seven-membered ring. Subsequent reaction of the enone with a Grignard reagent in ether/THF produces the saturated substituted ester derivative, which is reacted with aniline in the presence of a Lewis acid (AlCl₃), followed by acid in acetonitrile provides the substituted bicyclic phenamide.

In scheme II, the tricyclic phenamide is prepared from the N-boc protected enone using the benzyl-methoxymethyltrimethylsilylmethyl-amine or analogous substituted reagent to produce the N-substituted tricyclic intermediate which is subsequently reacted with analine in the presence of a Lewis acid (AlCl₃) in methylene chloride, followed by acid in acetonitrile to provide the substituted tricyclic phenamide. In scheme III, the substituted bicyclic phenamide is prepared from the ketone by introducing substitution in the position α to the ketone in the seven-membered ring using trimethylsilylchloride in the presence of triethylamine and sodium iodide in acetonitrile, followed by reaction of the ester with aniline in the presence of AlCl₃ (Lewis acid) in methylene chloride followed by acid in acetonitrile. Other approaches will be readily apparent to the person of ordinary skill in synthetic chemistry.

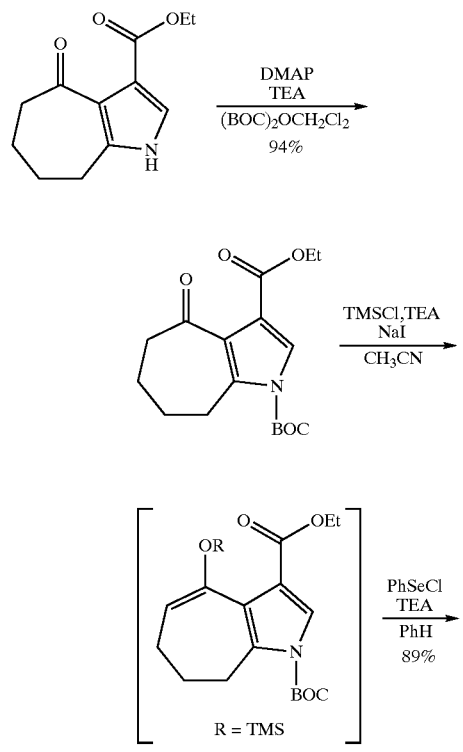

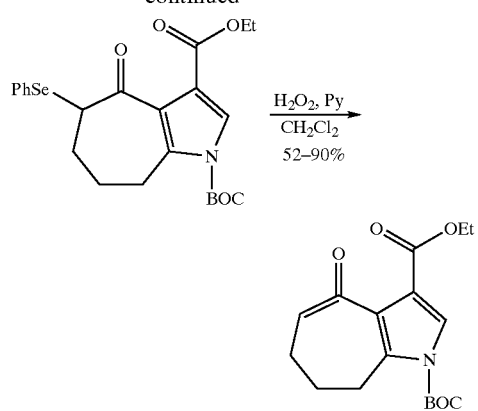

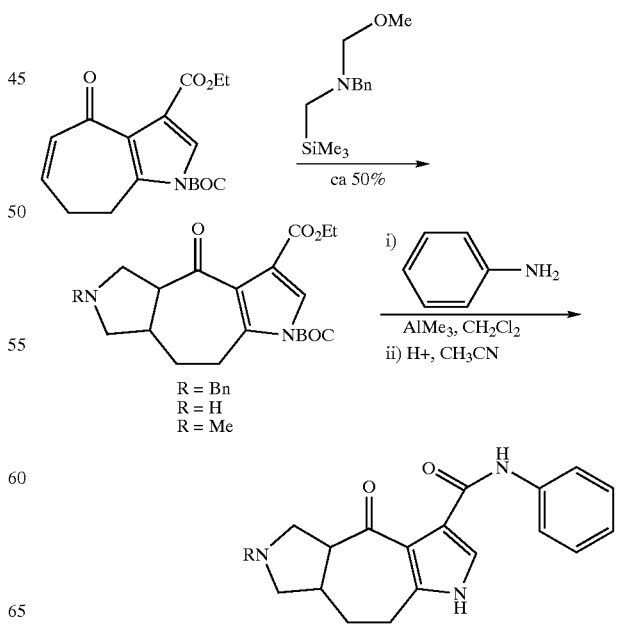

Scheme III

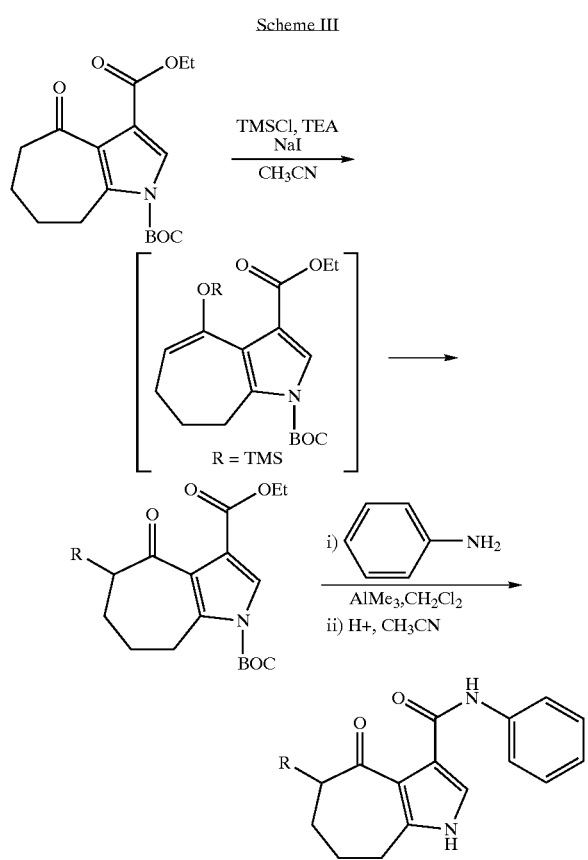

In pharmacological aspects of the present invention, the compounds of the present invention may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth, above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulas I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formulas I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to high solubility (preferably 500 ng/ml or more) in aqueous solutions, oral bioavailability, low toxicity, low serum protein binding, lack of clinically relevant EKG effects, and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention is now described by way of the following non-limiting examples.

EXAMPLES

Preparation of Starting Materials and Intermediates

The starting materials and various intermediates may be obtained from commercial sources, prepared from commercially available organic compounds, or prepared using well know synthetic methods. Unless otherwise specified standard, commercial grade reagents are used without further purification. Those having skill in the art will recognize that the starting materials may be varied and additional steps employed to produce compounds encompassed by the present inventions.

Representative examples of methods for preparing intermediates of the invention are set forth below.

Example 1

Preparation of 4-Oxo-7,8-dihydro-4H-cyclohepta[b]pyrrole-1,3-dicarboxylic acid 1-tert-butyl ester 3-ethyl ester

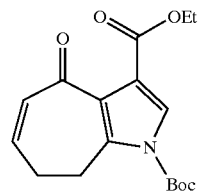

Step 1: 4-Trimethylsilanyloxy-7,8-dihydro-6H-cyclohepta[b]pyrrole-1,3-dicarboxylic acid 1-tert-butyl ester 3-ethyl ester

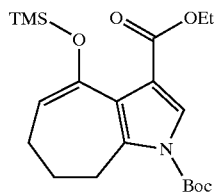

TMSCl (4.03 ml, 31.74 mmol) is added slowly to a solution of 4-oxo-5,6,7,8-tetrahydro-4H-cyclohepta[b]pyrrole-1,3-dicarboxylic acid 1-tert-butyl ester 3-ethyl ester (6.0 g, 18.67 mmol), NaI (4.76g, 31.74 mmol) and TEA (7.8 ml, 56 mmol) in $CH_3CN$ (100 ml) at room temperature. The reaction mixture is stirred at room temperature for 18 h. It is then quenched with saturated $NaHCO_3$ (aq., 70 ml). The layers are separated and the aqueous phase extracted with 1:1 EtOAC/hexanes. The organic layers are combined, dried ($Na_2SO_4$), and evaporated to afford the title compound as a brown oil. The title compound is used in the next step without further purification.

$^1$H NMR (400 MHz, $CDCl_3$) δ 0.12 (9H, s), 1.31 (3H, t), 1.59 (9H, s), 1.90 (2H, m), 2.02 (2H, m), 2.97 (2H, t), 4.25 (2H, q) 5.35 (1H, t), 7.62 (1H, s). MS ($ES^+$) 394 (M+1).

Step 2: 4-Oxo-5-phenylselanyl-5,6,7,8-tetrahydro-4H-cyclohepta[b]pyrrole-1,3-dicarboxylic acid 1-tert-butyl ester 3-ethyl ester

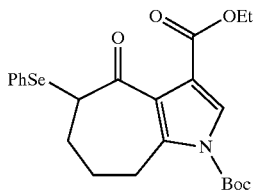

TEA (55.3 ml, 0.396 mol) is added to a solution of 4-trimethylsilanyloxy-7,8-dihydro-6Hcyclohepta[b]pyrrole-1,3-dicarboxylic acid 1-tert-butyl ester 3-ethyl ester (103.3 g, 0.264 mol) in benzene (1 L) at room temperature, followed by addition of PhSeCl (55.5 g, 0.29 mol) in benzene over 45 min. The reaction mixture is stirred at room temperature for 4 h. The solvent is removed in vacuo. The residue is purified by flash chromatograph (3:1 hexane/EtOAc) to provide the title compound as a light brown oil.

$^1$H NMR (400 MHz, $CDCl_3$) δ 0.86 (1H, t), 1.21 (3H, t), 1.58 (9H, s), 1.72 (1H, m), 1.82 (1H, m), 2.05 (1H, m), 2.35 (1H, m), 3.01–3.30 (2H, m), 4.20 (2H, q), 7.26 (3H, m), 7.63 (2H, m), 7.74 (1H, s). MS($ES^+$) 478 (M+1)

Step 3: 4-Oxo-7,8dihydro-4H-cyclohepta[b]pyrrole-1,3-dicarboxylic acid 1-tert-butyl ester 3-ethyl ester

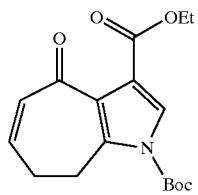

Pyridine (30 ml, 0.37 mol) is added to a solution of 4-oxo-5-phenylselanyl-5,6,7,8-tetrahydro-4H-cyclohepta[b]pyrrole-1,3-dicarboxylic acid 1-tert-butyl ester 3-ethyl ester (59 g, 0.124 mol) in $CH_2Cl_2$ at room temperature. A solution of $H_2O_2$ (30% in water, 225 ml) is then added dropwise. After the addition, reaction mixture is allowed to stir at room temperature for another hour and then quenched with saturated $NaHCO_3$ (aq., 250 ml). The aqueous layer is extracted with $CH_2Cl_2$ (10 ml×2), the organic layers combined, dried ($Na_2SO_4$) and evaporated. The residue is purified by chromatograph to provide the title compound as yellow solid. $^1$H NMR (400 MHz, $CDCl_3$) δ 1.30 (3H, t), 1.58 (9H, s), 2.55 (2H, m), 3.40 (2H, t), 4.31 (2H, q), 6.19 (1H, d), 6.60 (1H, m), 7.48 (1H, s). MS ($ES^+$) 320 (M+1)

Example 2

Preparation of 6-Methyl-4-oxo-1,4,5,6,7,8-hexahydro-cydohepta[b]pyrrole-3-carboxylic acid pyridin-2-ylamide

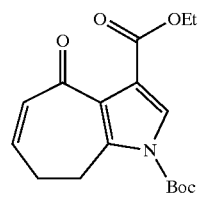

Step 1: 6-Methyl-4-oxo-5,6,7,8-tetrahydro-4H-cyclohepta[b]pyrrole-1,3-dicarboxylic acid 1-tert-butyl ester 3-ethyl ester

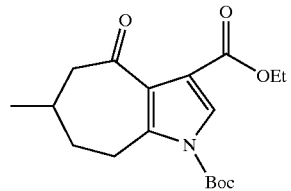

MeLi (1.4M in ether, 2 ml) is added dropwise to a stirred suspension of CuI (268 mg, 1.40 mmol) in $Et_2O$ at 0° C. The reaction mixture is kept at 0° C. for 15 min. 4-oxo-7,8-dihydro-4H-cyclohepta[b]pyrrole-1,3-dicarboxylic acid 1-tert-butyl ester 3-ethyl ester (300 mg, 0.94 mmol) in THF is added slowly to the solution at 0° C., the reaction mixture is allowed to warm up to room temperature over a period of 30 min and then quenched with saturated $NH_4Cl$(aq., 30 ml). 50 ml $Et_2O$ is added and stirring is continued for 5 min. The layers are separated; the organic layer is washed with water (20 ml), dried ($Na_2SO_4$), and evaporated. Flash chromatography (30% EtOAc/hexanes) provides the title compound as white powder. $^1$H NMR (400 MHz, $CDCl_3$) δ 1.02 (3H, d), 1.28 (3H, t), 1.56 (9H+1H, s+m), 1.92 (1H, m), 2.15 (1H, m), 2.48 (1H, q), 2.80 (1H, q), 3.15–3.25 (2H, m), 4.24 (2H, q), 7.57 (1H, s). MS ($ES^+$) 336 (M+1)

Step 2: 6-Methyl-4-oxo-1,4,5,6,7,8-hexahydro-cyclohepta[b]pyrrole-3-carboxylic acid ethyl ester

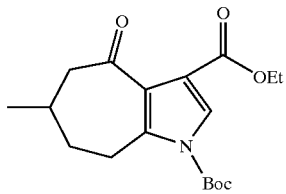

6-Methyl-4-oxo-5,6,7,8-tetrahydro-4H-cyclchepta[b]pyrrole-1,3-dicarboxylic acid 1-tert-butyl ester 3-ethyl ester (273 mg, 0.814 mmol) is dissolved in 1:1 mixture of TFA and CH$_2$Cl$_2$ (4 ml). The reaction mixture is stirred at room temperature for 3 h. Solvents a re removed in vacuo and the residue is put on a column (1:1 EtOAc/hexanes) to provide the title compound as white solid. $^1$H NMR (400 MHz, CDCl$_3$) δ 1.01 (3H, d), 1.26 (3H, t), 1.1.50 (1H, m), 1.96 (1H,m), 2.12 (1H, m), 2.54 (1H, q), 2.70–2.90 (3H, m), 4.20 (2H, q), 7.17 (1H, s). MS (ES$^+$) 236 (M+1)

Step 3: 6-Methyl-4-oxo-1,4,5,6,7,8-hexahydro-cyclohepta[b]pyrrole-3-carboxylic acid pyridin-2-ylamide

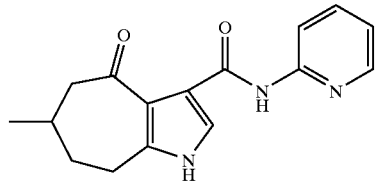

AlMe$_3$ (2M in toluene, 0.85 ml, 1.7 ml) is added dropwise to 2-aminopyridine (199.9 mg, 2.12 mmol) in CH$_2$Cl$_2$ at 0° C. The reaction mixture is stirred at room temperature for 0.5 h, it is then transferred to a solution of 6-methyl-4-oxo-1,4,5,6,7,8-hexahydro-cyclohepta[b]pyrrole-3-carboxylic acid ethyl ester (100 mg, 0.425 mmol) in CH$_2$Cl$_2$, via syringe. The reaction mixture is heated at 40° C. for 10 h. 5 ml water is added, stirring continued for 10 min. The solid residue is filtered off with celite, the layers separated, the aqueous phase extracted with CH$_2$Cl$_2$ (10 ml×2), and the combined organic phases are dried (Na$_2$SO$_4$) and evaporated.

The residue obtained from last step is dissolved in CH$_3$CN (2 ml) and saturated NaH$_2$PO$_4$ (aq., 4 ml). The reaction mixture is stirred at room temperature for 5 h. The solution is basified with saturated NaHCO$_3$ (aq.), and 10 ml CH$_2$Cl$_2$ are added. Layers separated, aqueous phase was extracted with CH$_2$Cl$_2$ (10 ml×2). Combined organic phases are dried (Na$_2$SO$_4$) and evaporated. Flash chromatography (60% EtOAc/hexanes) provides the title compound as white powder. This compound may be salted as HCl salt. $^1$H NMR (400 MHz, CD$_3$OD) δ 1.1.05 (3H, d), 1.45 (1H, m), 2.06–2.17 (2H, m), 2.70 (1H, m), 2.80–3.01 (3H, m), 7.07 (1H, q), 7.51 (1H, s), 7.75 (1H, m), 8.22 (1H, d), 8.28 (1H, m). MS (ES$^+$) 284 (M+1)

Example 3

Preparation of 6-Isopropyl-4-oxo-1,4,5,6,7,8-hexahydro-cyclohepta[b]pyrrole-3-carboxylic acid pyridin-2-ylamide

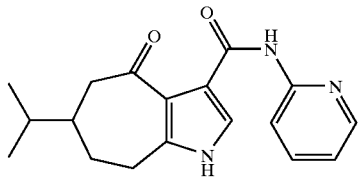

Step 1: 6-Methyl4-oxo-1,4,5,6,7,8-hexahydro-cyclohepta[b]pyrrole3-carboxylic acid pyridin-2-ylamide

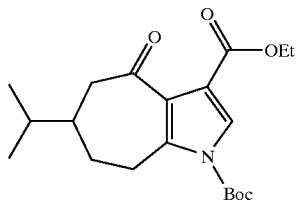

The title compound may be obtained as a white solid by the method described in Example 2, Step 1, using isopropylmagnesium chloride as the organometallic reagent. $^1$H NMR (400 MHz, CDCl$_3$) δ 0.89 (6H, m), 1.28 (3H, t), 1.56 (9H+2H, s+m), 1.78 (1H, m), 1.97 (1H, m), 2.60 (1H, q), 2.75 (1H, m), 3.19 (2H, m), 4.25 (2H, q), 7.59 (1H, s). MS (ES$^+$) 364 (M+1)

Step 2: 6-Isopropyl-4-oxo-1,4,5,6,7,8-hexahydro-cyclohepta[b]pyrrole-3-carboxylic acid ethyl ester

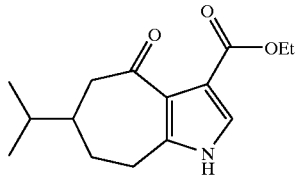

The title compound may be obtained as white solid by the methods described in Example 2, Step 2. $^1$H NMR (400 MHz, CDCl$_3$) δ 0.87 (6H, m), 1.25 (3H, t), 1.60 (2H, m), 1.75 (1H, m), 1.89 (1H, m), 2.64 (2H, m), 2.88 (2H, m), 4.20 (2H, q), 7.20 (1H, s). MS (ES$^+$) 264 (M+1)

Step 3 6-Isopropyl4oxo-1.4,5,6,7,8-hexahydro-cyclohepta[b]pyrrole-3-carboxylic acid pyridin-2-ylamide

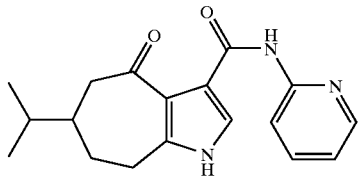

The title compound may be obtained as a white solid and salted as HCl salt by the methods given in Example 2, Step 3. $^1$H NMR (400 MHz, CD$_3$OD) δ 0.97 (6H, m), 1.65 (2H, m), 1.70 (1H, m), 2.01 (1H, m), 2.72–2.90 (4H, m), 7.07 (1H, q), 7.51 (1H, s), 7.75 (1H, m), 8.22 (1H, d), 8.28 (1H, m). MS (ES$^+$) 312 (M+1).

Example 4

Preparation of 6-(4-Fluoro-phenyl)-4-oxo-1,4,5,6,7,8-hexahydrocyclohepta[b]pyrrole-3-carboxylic acid pyridin-2-ylamide

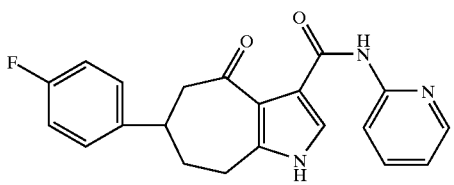

Step 1: 6-(4-Fluoro-phenyl)-4-oxo-5,6,7,8-tetrahydro-4H-cyclohepta[b]pyrrole-1,3-dicarboxylic acid 1-tert-butyl ester 3-ethyl ester

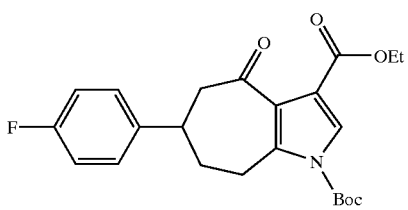

The title compound may be obtained as a slightly colored solid by the methods described in Example 2, Step 1. $^1$H NMR (400 MHz, COCl$_3$) δ 1.27 (3H, t), 1.59 (9H, s), 2.07 (1H, m), 2.20 (1H, m), 2.92–3.37 (5H, m), 4.24 (2H, q), 6.93 (2H, m), 7.14 (2H, m), 7.63 (1H, s). MS (ES$^+$) 416 (M+1)

Step 2: 6-(4-Fluoro-phenyl)-4-oxo-1,4,5,6,7,8-hexahydro-cyclohepta[b]pyrrole-3-carboxylic acid ethyl ester

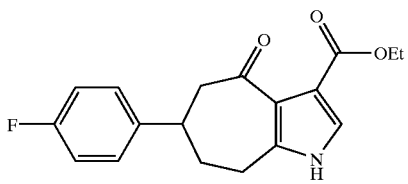

The title compound (190 mg, 74%) may be obtained as white powder by the procedure described in Example 2, Step 2. $^1$H NMR (400 MHz, CDCl$_3$) δ 1.26 (3H, t), 1.95 (1H, m), 2.19 (1H, m), 2.85–3.00 (4H, m), 3.18 (1H, m), 4.23 (2H, q), 6.93 (2H, m), 7.11 (2H, m), 7.21 (1H, s). MS (ES$^+$) 316(M+1).

Step 3: 6-(4-Fluoro-phenyl)4-oxo-1,4,5,6,7,8-hexahydro-cyclohepta[b]pyrrole-3-carboxylic acid pyridin-2-ylamide

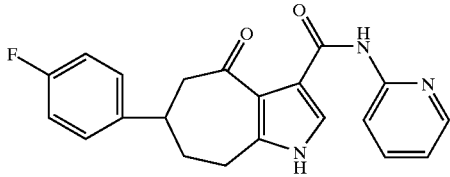

The title compound may be obtained as white solid and salted as HCl salt by the methods described in Example 2, Step 3, $^1$H NMR (400 MHz, CD$_3$OD) δ 1.95 (1H, m), 2.31 (1H, m), 3.02 (2H, m), 3.19 (3H, m), 6.99 (2H, m), 7.07 (1H, m), 7.26 (2H, m), 7.40 (1H, m), 7.56 (1H, s), 7.78 (1H, m), 7.83 (1H, m), MS (ES$^+$) 364 (M+1).

Example 5

Preparation of 6-(3-Fluoro-4-methoxy-phenyl)-4-oxo-1,4,5,6,7,8-hexahydro-cyclohepta[b]pyrrole-3carboxylic acid pyridin-2-ylamide

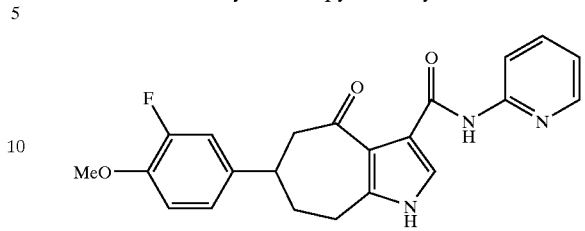

Step 1: 6-(3-Fluoro-4-methoxy-phenyl)-4-oxo-5,6,7,8-tetrahydro-4H-cyclohepta[b]pyrrol-1,3-dicarboxylic acid 1-tert-butyl ester 3ethyl ester

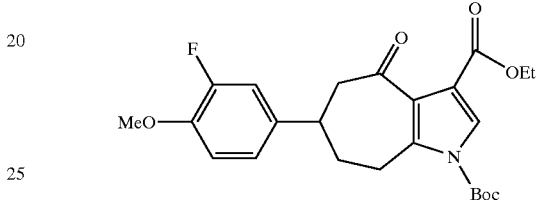

The title compound may be obtained as a white solid by the procedures described in Example 2, Step 1, $^1$H NMR (400 MHz, CDCl$_3$) δ 1.28 (3H, t), 1.57 (9H, s), 2.01(1H, m), 2.19 (1H, m), 2.89–3.35 (5H, m), 3.83 (3H, s), 4.25 (2H, q), 6.83–6.95 (3H, m), 7.62 (1H, s). MS (ES$^+$) 446 (M+1)

Step 2: 6-(3-Fluoro-4-methoxy-phenyl)-4-oxo-1,4,5,6,7,8-hexahydro-cyclohepta[b]pyrrole-3-carboxylic acid ethyl ester

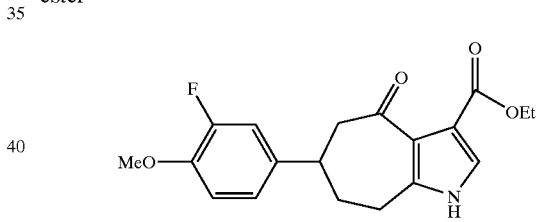

The title product was obtained as white solid by the methods described in Example 2, Step 2. $^1$H NMR (400 MHz, CDCl$_3$) δ 1.26 (3H, t), 1.96 (1H, m), 2.17 (1H, m), 2.84–3.12 (5H, m), 3.82 (3H, s), 4.09 (2H, q), 6.80–6.91 (3H, m), 7.20 (1H, s). MS (ES$^+$) 346 (M+1).

Step 3: 6-(3-Fluoro-4-methoxy-phenyl)-4-oxo-1,4,5,6,7,8-hexahydro-cyclohepta[b]pyrrole-3-carboxylic acid pyridin-2-ylamide

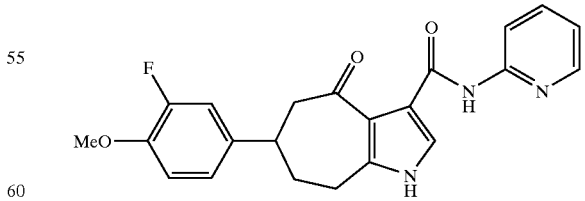

The title compound may be obtained as white solid and salted as HCl salt by the methods described in Example 2, Step 3. $^1$H NMR (400 MHz, CD$_3$OD) δ 1.90 (1H, m), 2.28 (1H, m), 2.94–3.20 (5H, m), 3.80 (3H, s), 6.95–7.08 (4H, m), 7.56 (1H, s), 7.75 (1H, t), 8.12 (2H, m). MS (ES$^+$) 394 (M+1)

Example 6

Preparation of 6-Benzyl-4-oxo-4,4a,5,6,7,7a,8,9-octahydro-1H-1,6-diaza-cyclopenta[f]azulene-3-carboxylic acid pyridin-2-ylamide

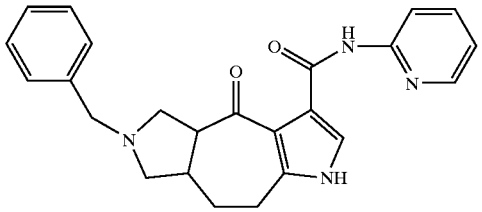

Step 1: 6-Benzyl-4-oxo-4,4a,5,6,7,7a,8,9-octahydro-1,6-diaza-cyclopenta[f]azulene-1,3-dicarboxylic acid 1-tert-butyl ester 3-ethyl ester

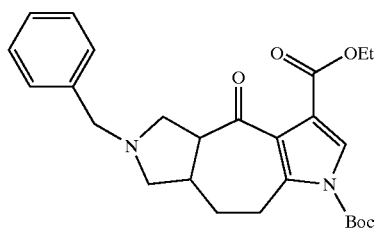

4-Oxo-7,8-dihydro-4H-cyclohepta[b]pyrrole-1,3-dicarboxylic acid 1-tert-butyl ester 3-ethyl ester (2.92 g, 9.15 mmol), LiF (296 mg, 11.4 mmol) and benzyl-methoxymethyl-trimethylsilanylmethyl-amine are mixed together in CH$_3$CN (10 ml). The reaction mixture is sonicated under N$_2$. The water bath is kept under 35° C. with ice. After 6 h, solvents are removed in vacuo. The residue is put on a column (1:1 EtOAc hexanes) to afford the title compound as clear oil, which solidified upon standing. $^1$H NMR (400 MHz, CDCl$_3$) δ 1.23 (3H, t), 1.56 (9H, s), 1.88–2.00 (2H, m), 2.65 (1H, m), 2.92–3.02 (4H, m), 3.24 (1H, m), 3.50–3.59 (3H, m), 4.06 (1H, q), 4.19 (2H, q), 7.18–7.27 (5H, m), 7.62 (1H, s). MS (ES$^+$) 453 (M+1)

Step 2: 6-Benzyl4-oxo-4,4a,5,6,7,7a,8,9-octahydro-1H-1,6-diaza-cyclopenta[f]azulene-3-carboxylic acid pyridin-2-ylamide

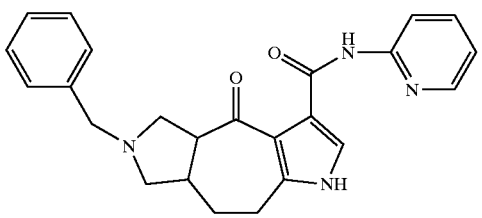

6-Benzyl-4oxo-4,4a,5,6,7,7a,8,9-octahydro-1,6-diaza-cyclopenta[f]azulene-1,3-dicarboxylic acid 1-tert-butyl ester 3-ethyl ester (350 mg, 0.773 mmol) are used for the amination reaction. The amination is carried out via the methods described in Example 2, Step 3. The crude products are used in the next step without further purification.

The crude products obtained from step a) are dissolved in a 1:1 mixture of TFA and CH$_2$Cl$_2$ (4 ml). The reaction mixture is stirred at room temperature for 3 h. The solvents are removed in vacuo and the residue was put on a column (4% MeOH/CH$_2$Cl$_2$) to provide the title compound as white solid. This compound is salted as an HCl salt. $^1$H NMR (400 MHz, CD$_3$OD) δ 1.88–2.00 (2H, m), 2.55 (1H, m), 2.92–3.02 (4H, m), 3.34 (1H, m), 3.50–3.59 (3H, m), 3.95 (1H, m), 6.95 (1H, m), 7.18–7.26 (5H, m), 7.61 (2H, m), 8.35 (2H, m). MS (ES$^+$) 401 (M+1)

Example 7

Preparation of 4-Oxo-4,4a,5,6,7,7a,8,9-octahydro-1H-1,6-diaza-cyclopenta[f]azulene-3-carboxylic acid pyridin-2-ylamide

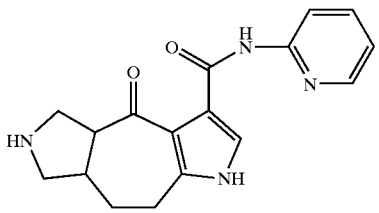

Pd(OH)$_2$ (Pearlman's catalyst, 30 mg) is added to a solution of 6-benzyl-4-oxo-4,4a,5,6,7,7a,8,9-octahydro-1H-1,6-diaza-cyclopenta[f]azulene-3-carboxylic acid pyridin-2-ylamide (65 mg, 0.16 mmol) and HCOONH$_4$ (204 mg, 3.24 mmol) in EtOH (10 ml). The reaction mixture is heated at 78° C. for 20 min. Pd catalyst is filtered off with celite. The solvent is removed by rotavapor. The residue is loaded on a column (0.5% TEA+19.5% MeOH+80% CH$_3$CN) to provide the title compound (20 mg, 40%) as white solid. This compound may be salted as HCl salt. $^1$H NMR (400 MHz, CD$_3$OD) δ 1.98 (1H, m), 2.01–2.16 (2H, m), 2.65 (1H, m), 3.02–3.25 (5H, m), 3.76 (1H, m), 7.09 (1H, m), 7.57 (1H, s), 7.78 (1H, m), 8.27 (2H, m). MS (ES$^+$) 311 (M+1)

Example 8

Preparation of 6-Methyl-4-oxo-4,4a,5,6,7,7a,8,9-octahydro-1H-1,6-diaza-cyclopenta[f]azulene-3-carboxylic acid pyridin-2-ylamide

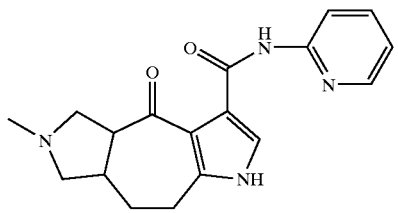

Step 1: 6-Methyl-4-oxo-4,4a,5,6,7,7a,8,9octahydro-1,6-diaza-cyclopenta[f]azulene-1,3-dicarboxylic acid 1-tert-butyl ester 3-ethyl ester

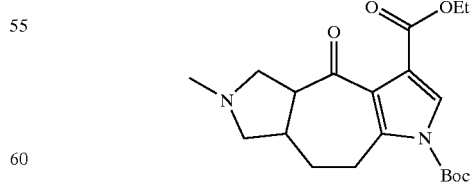

MeI (5.7 mL, 93 mmol) is added to 6-benzyl4-oxo-4,4a,5,6,7,7a,8,9-octahydro-1,6-diaza-cyclopenta[f]azulene-1,3-dicarboxylic acid 1-tert-butyl ester 3-ethyl ester (2.8 g, 6.2 mmol) in acetone (100 mL) at room temperature. The reaction mixture is stirred at room temperature for 4 h. The solvent and excessive MeI are removed under reduced pressure. The resulting solid is used in the next step without further purification.

The solid obtained above is dissolved in EtOH (700 mL). Pd/C (1 g, 10% Pd on activated carbon) is added. The reaction mixture was shaken under $H_2$ (40 psi) at 65–70° C. for 10 h. Pd/C is filtered off with Celite. EtOH is removed under reduced pressure. The residue was loaded on a column (9:1:1 $CH_2Cl_2/MeOH/NH_4OH$) to provide the title compound (1.15 g, 40%) as slightly colored solid. $^1$H NMR (400 MHz, $CD_3OD$) □ 7.68 (1H, s), 4.17 (2H, q), 3.60 (1H, m), 3.31 (1H, m), 3.06–2.68 (4H, m), 2.34 (3H, s), 2.03–1.97 (2H, m), 1.58 (9H, s), 1.25 (3H, t). MS ($ES^+$) 377 (M+1).

Step 2: 6-Methyl-4-oxo-4,4a,5,6,7,7a,8,9-octahydro-1H-1,6-diaza-cyclopenta[f]azulene-3-carboxylic acid pyridin-2-ylamide.

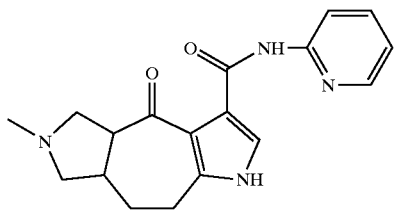

(a) Methyl-4-oxo-4,4a,5,6,7,7a,8,9-octahydro-1,6-diaza-cyclopenta[f]azulene-1,3-dicarboxylic acid 1-tert-butyl ester 3-ethyl ester (150 mg, 0.398 mmol) is used for the amination reaction. The amination reaction is carried out in the same way as described in Example 2, Step 3. The crude products are put into next step without further purification.

(b) The crude products obtained from the previous step are dissolved in 1:1 mixture of TFA and $CH_2Cl_2$ (4 ml). The reaction mixture is stirred at room temperature for 3 h. The solvents are removed under reduced pressure, and the residue was put on a column (4% $MeOH/CH_2Cl_2$) to provide the title compound (52 mg, 40%) as white solid. It title compound may be salted as HCl salt. $^1$H NMR (400 MHz, $CD_3OD$); δ 8.29–8.23 (2H, m), 7.76 (1H, m), 7.58 (1H, s), 7.08 (1H, m), 3.65 (1H, m), 3.37–2.99 (4H, m), 2.77 (1H, m), 2.48 (1H, m), 2.43 (3H, s), 2.29 (1H, m), 2.04 (1H, m), 1.79 (1H, m). MS ($ES^+$) 325 (M+1)

Example 9

Preparation of 6-Dimethylaminomethyl-4-oxo-1,4,5,6,7,8-hexahydro-cyclohepta[b]pyrrole-3-carboxylic acid pyridin-2-ylamide

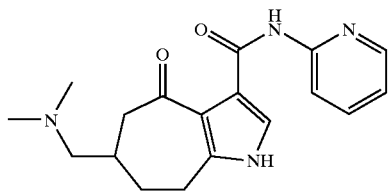

Step 1: 6-Nitromethyl-4-oxo-1,4,5,6,7,8-hexahydro-cyclohepta[b]pyrrole-3-carboxylic acid ethyl ester

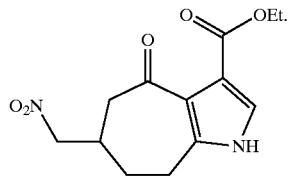

4-Oxo-7,8-dihydro-4H-cyclohepta[b]pyrrole-1,3-dicarboxylic acid 1-tert-butyl ester 3-ethyl ester (6.81 g, 21.3 mmol) is dissolved in $CH_3NO_2$ (50 ml), Triton B (40% aqueous, 2.5 mL) is added quickly. The reaction mixture was kept at 80° C. for 8 h. The mixture is cooled and the solvent removed under reduced pressure. The residue is taken into 50 ml $CH_2Cl_2$ and 25 ml $H_2O$. The aqueous phase is adjusted to slightly basic with 1N HCl and sat. $NaHCO_3$, and extracted with $CH_2Cl_2$ (30 mL×4). Organic phases are combined, dried ($Na_2SO_4$), and evaporated. Flash chromatography (1:1 hexanes/EtOAc) provides the title compound (5.6 g, 93%) as white solid. $^1$H NMR (400 MHz, $CD_3OD$) δ 7.21 (1H, s), 4.45 (2H, d), 4.20 (2H, q), 2.97–2.62 (5H, m), 2.04 (1H, m), 1.65 (1H, m), 1.27 (3H, t). MS ($ES^+$) 281 (M+1)

Step 2: Dimethylaminomethyl4-oxo-1,4,5,6,7,8-hexahydro-cyclohepta[b]pyrrole-3-carboxylic acid ethyl ester.

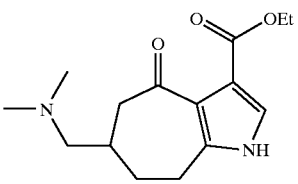

6-Nitromethyl-4-oxo-1,4,5,6,7,8-hexahydro-cyclohepta[b]pyrrole-3-carboxylic acid ethyl ester (350 mg, 1.25 mmol) is dissolved in EtOH/THF (50 mL/13 mL). Raney-Ni (50% aqueous slurry, 350 mg) and HCHO (37% in $H_2O$, 2.04 g, 25 mmol) are added to the solution. The reaction mixture is shaken under $H_2$ (40 psi) at room temperature for 24 h. The catalyst is filtered off with Celite and the solvents are removed under reduced pressure. Flash chromatography (4% MeOH+95% $CH_2Cl_2$+1% $NH_4OH$) provides the title compound (180 mg, 52%) as white solid. $^1$H NMR (400 MHz, $CD_3OD$) δ 7.32 (1H, s), 4.18 (2H, q), 3.01–2.75 (3H, m), 2.54 (1H, m), 2.26–2.17 (9H, m), 2.02 (1H, m), 1.57 (1H, m), 1.25 (3H, t). MS ($ES^+$) 279 (M+1)

Step 3: 6-Dimethylaminomethyl-4oxo-1,4,5,6,7,8-hexahydro-cyclohepta[b]pyrrole-3-carboxylic acid pyridin-2-ylamide

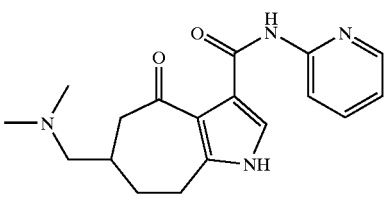

In the same way as described in Example 2, Step 3, the title compound (125 mg, 50%) is obtained as a white solid. It may be salted as an HCl salt. $^1$H NMR (400 MHz, $CD_3OD$) δ 8.31–8.24 (2H, m), 7.79 (1H, m), 7.54 (1H, s), 7.10 (1H, m), 3.04–2.73 (4H, m), 2.28–2.18 (9H, m), 2.07 (1H, m), 1.56 (1H, m). MS ($ES^+$) 327 (M+1)

Example 10

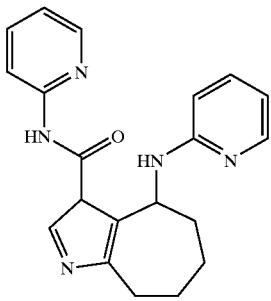

4-(Pyridin-2-ylamino)-3,4,5,6,7,8-hexahydro-cyclohepta[b]pyrrole-3-carboxylic acid pyridin-2-ylamide This compound is prepared by the reductive amination of the imine (Schiff Base) which is prepared by reaction of the corresponding unsubstituted ketone (see example 1, step 1 with minor modification) with 2-aminopyridine. Reduction of the resulting imine using standard reduction conditions (LiAlH$_4$, NaBH$_4$, sodium acetoxy borohydride, H$_2$/catalyst) affords the above compound. The preferred reducing agent is sodium acetoxy borohydride. These compounds have limited stability due to the presence of the secondary amine group. Other compounds, similar to the above compound (having an amine substituent on the seven-membered ring) may be synthesized using modifications of the disclosed methods.

Example 11

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^{3}$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 12

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 13

Binding Assay

The high affinity and high selectivity of compounds of this invention for the benzodiazepine site of the GABA$_A$ receptor was confirmed using the binding assay described by Thomas and Tallman (J. Bio. Chem. 1981; 156:9838–9842, and J. Neurosci. 1983; 3:433–440).

Rat cortical tissue was dissected and homogenized in 25 volumes (w/v) of Buffer A (0.05 M Tris HCl buffer, pH 7.4 at 4° C.). The tissue homogenate was centrifuged in the cold (4° C.) at 20,000×g for 20 minutes. The supernatant was decanted, the pellet rehomogenized in the same volume of buffer, and centrifuged again at 20,000×g. The supernatant of this centrifugation step was decanted and the pellet stored at −20° C. overnight. The pellet was then thawed and resuspended in 25 volumes of Buffer A (original wt/vol), centrifuged at 20,000×g and the supernatant decanted. This wash step was repeated once. The pellet was finally resuspended in 50 volumes of Buffer A.

Incubations contained 100 μl of tissue homogenate, 100 μl of radioligand, (0.5 nM $^{3}$H-Ro15-1788 [$^{3}$H-Flumazenil], specific activity 80 Ci/mmol), and test compound or control (see below), and were brought to a total volume of 500 μl with Buffer A. Incubations were carried for 30 min at 4° C. and then rapidly filtered through Whatman G F B filters to separate free and bound ligand. Filters were washed twice with fresh Buffer A and counted in a liquid scintillation counter. Nonspecific binding (control) is determined by displacement of $^{3}$H Ro15-1788 with 10 μM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve was obtained with up to 11 points spanning the compound concentration range from $10^{-12}$M to $10^{-5}$M obtained per curve by the method described above for determining percent inhibition. K$_i$ values were calculated according the Cheng-Prussof equation. Each of the compounds set forth in Examples 1–10 as compounds was tested in this fashion and each was found to have a K$_i$ of <4 μM. Preferred compounds of the invention exhibit K$_i$ values of less than 100 nM and more preferred compounds of the invention exhibit K$_i$ values of less than 10 nM.

The results for the above-described compounds in the binding assay are presented below.

Example 2: 2 nM
Example 3: 1 nM
Example 4: 7 nM
Example 5: 8 nM
Example 6: 4 nM
Example 7: 7 nM
Example 8: 8 nM
Example 9: 23 nM
Example 10: 24 nM

Example 14

Electrophysiology

The following assay is used to determine if a compound of the invention acts as an agonist, an antagonist, or an inverse agonist at the benzodiazepine site of the GABA$_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. Xenopus Laevis oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_2\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$. GENBANK accession no. L08497. For each subunit combination, sufficient message for each constituent subunit is injected to provide current amplitudes of >10 nA when 1 $\mu$M GABA is applied.

Compounds are evaluated against a GABA concentration that evokes <10% of the maximal evokable GABA current (e.g. 1 $\mu$M–9 $\mu$M). Each oocyte is exposed to increasing concentrations of a compound being evaluated (test compound) in order to evaluate a concentration/effect relationship. Test compound efficacy is calculated as a percent-change in current amplitude: $100*((Ic/I)-1)$, where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 $\mu$M RO15-1788, followed by exposure to GABA+1 $\mu$M RO15-1788 +test compound. Percent change due to addition of compound is calculated as described above. Any percent change observed in the presence of RO15-1788 is subtracted from the percent changes in current amplitude observed in the absence of 1 $\mu$M RO15-1788. These net values are used for the calculation of average efficacy and $EC_{50}$ values by standard methods. To evaluate average efficacy and $EC_{50}$ values, the concentration/effect data are averaged across cells and fit to the logistic equation.

It is to be understood that the foregoing describes preferred embodiments of the present invention and that modifications may be made therein without departing from the scope of the present invention as set forth in the following claims.

What is claimed is:
1. A compound of the formula

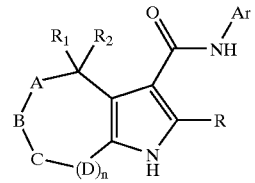

or a pharmaceutically acceptable salt thereof, wherein:
R is selected from halogen, cyano, nitro, and amino;
$R_1$ is chosen from amino, fluoro, hydroxy, $C_1$–$C_6$ alkoxy, arylamino, heteroarylamino, aryloxy, or heteroaryvoxy, and
$R_2$ is chosen from hydrogen, fluoro, $C_1$–$C_6$ alkyl, and aryl($C_1$–$C_4$alkyl); or
$R_1$ and $R_2$ together represent an oxo group; or
$R_1$ and $R_2$ are joined to form a saturated, or partially unsaturated ring of from 4 to 8 members containing 1 or more heteroatoms independently chosen from N, S, and O;
n is 0, 1, or 2;
A is chosen from O, $NR_3$, and $CR_3·R_{3''}$;
B is chosen from O, $NR_4$, and $CR_4·R_{4''}$;
C is chosen from O, $N_5$, and $CR_5·R_{5''}$;
D is independently chosen at each occurrence from O, $N_6$, and $CR_{6'}R_{6''}$;
$R_3$, $R_4$, $R_5$, and $R_6$ are independently chosen at each occurrence from hydrogen, $C_1$–$C_6$ alkyl$_1$, $C_2$–$C_6$alkenyl$_1$, $C_2$–$C_6$alkynyl$_1$, $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$,), hydroxy($C_1$–$C_6$ alkyl$_1$), amino($C_2$–$C_6$ alkyl$_1$), aryl$_1$, aryl$_1$($C_1$–$C_4$alkyl$_1$), heteroaryl$_1$, and heteroaryl$_1$($C_1$–$C_4$alkyl$_1$);
$R_{3'}$, $R_{3''}$, $R_{4'}$, $R_{4''}$, $R_{5'}$, $R_{5''}$, $R_{6'}$, and $R_{6''}$ are independently chosen at each occurrence from hydrogen, halogen, hydroxy, amino, cyano, nitro, oxo, $C_1$–$C_6$ alkyl$_1$, $C_1$–$C_6$ alkoxy$_1$, $C_2$–$C_6$alkenyl$_1$, $C_2$–$C_6$alkynyl$_1$, $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$), halo($C_1$–$C_6$)alkyl$_1$, halo($C_1$–$C_6$)alkoxy$_1$ hydroxy($C_1$–$C_6$ alkyl$_1$), amino($C_1$–$C_6$ alkyl$_1$), mono- or di($C_1$–$C_6$alkyl$_1$)amino, mono- or di($C_1$–$C_6$alkyl$_1$)amino($C_1$–$C_6$alkyl$_1$), aryl$_1$, aryl$_1$($C_1$–$C_4$alkyl$_1$), heteroaryl$_1$, and heteroaryl$_1$($C_1$–$C_4$alkyl$_1$);
wherein each alkyl$_1$, alkenyl$_1$, alkynyl$_1$, alkoxy$_1$, cydoalkyl$_1$, heterocycloalkyl$_1$, aryl$_1$, and heteroaryl$_1$ is unsubstituted or substituted with one or more subsfituents selected from: hydroxy, oxo, halogen, amino, cyano, nitro, $C_1$–$C_6$alkyl, $C_1$–$C_6$alkoxy, and mono- or di-($C_1$–$C_6$alkyl)amino; with the proviso that
a) at least one of B, C, and D is nitrogen and is substituted by $C_3$–$C_7$cycloalkyl$_1$, $C_3$–$C_7$cycloalkyl$_1$($C_1$–$C_4$alkyl$_1$), heterocycloalkyl$_1$, heterocydoalkyl$_1$($C_1$–$C_4$alkyl$_1$), hydroxy($C_1$–$C_6$ alkyl$_1$), amino($C_1$–$C_6$ alkyl$_1$), aryl$_1$, aryl$_1$($C_1$–$C_4$alkyl$_1$), heteroaryl$_1$, and heteroaryl$_1$($C_1$–$C_4$alkyl$_1$), or
b) at least one of B, C, and D are carbon and is substituted by halogen, hydroxy, amino, cyano, nitro, oxo, $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$), halo($C_1$–$C_6$)alkyl$_1$, halo($C_1$–$C_6$)alkoxyl$_1$, hydroxy($C_1$–$C_6$ alkyl$_1$), amino($C_1$–$C_6$ alkyl$_1$), mono- or di($C_1$–$C_6$alkyl$_1$)amino, mono- or di($C_1$–$C_6$alkyl$_1$) amino($C_1$–$C_6$alkyl$_1$), aryl$_1$, aryl$_1$($C_1$–$C_4$alkyl$_1$), heteroaryl$_1$, and heteroaryl$_1$($C_1$–$C_4$alkyl$_1$), or c) A is carbon and is substituted by halogen, hydroxy, amino, cyano, nitro, oxo, $C_1$–$C_6$alkoxy, halo($C_1$–$C_6$) alkyl$_1$, halo($C_1$–$C_6$)alkoxy$_1$, hydroxy($C_1$–$C_6$ alkyl$_1$), or d) n is 1 or 2 and at least one of B, C, or D is nitrogen or oxygen; or any of $R_{3'}$ and $R_{3''}$, $R_{4'}$ and $R_{4''}$, $R_{5'}$ and $R_{5''}$, and $R_{6'}$, and $R_6$ may be joined to form a saturated, partially unsaturated, or unsaturated carbocyclic or heterocyclic ring$_1$;

wherein said ring$_1$ is a saturated, partially unsaturated, or unsaturated carbocyclic or heterocyclic ring of from 3–8 ring members which contains 0, 1, or 2 heteroatoms independently chosen from O, N, and S, and said ring, is unsubstituted or is substituted by 1, 2, or 3 substituents independently chosen from halogen, hydroxy, amino, cyano, nitro, oxo, $C_1$–$C_6$ alkyl, $C_1$–$C_6$ alkoxy, $C_2$–$C_6$alkenyl, $C_2$–$C_6$alkynyl, halo($C_1$–$C_6$) alkyl, halo($C_1$–$C_6$)alkoxy hydroxy($C_1$–$C_6$ alkyl), amino($C_1$–$C_6$ alkyl), mono- or di($C_1$–$C_6$alkyl)amino, and mono- or di($C_1$–$C_6$alkyl)amino($C_1$–$C_6$alkyl);

Ar is a group of the formula

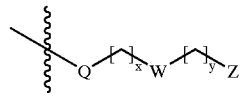

Q is an optionally substituted carbocyclic aryl or optionally substituted heteroaryl group having from 1 to 3 rings, 5 to 6 members in each ring and from 1 to 3 heteroatoms;

W is oxygen, nitrogen, sulfur, or $CR^7R^8$ where $R^7$ and $R^8$ are the same or different and represent hydrogen, $C_1$–$C_6$ alkyl, or $R^7$ and $R^8$ may be taken together to represent a cyclic moiety having 3–7 carbon atoms;

Z is hydrogen, hydroxy, $C_1$–$C_6$ alkoxy, $C_3$–$C_7$ cycloalkyl, $C_3$–$C_7$ cycloalkyl($C_1$–$C_4$alkoxy), amino, mono or di($C_1$–$C_6$alkyl)amino, or $NR^9COR^{10}$ where $R^9$ and $R^{10}$ are the same or different and represent hydrogen or $C_1$–$C_6$ alkyl, or $R^9$ and $R^{10}$ may be joined to from a $C_3$–$C_7$ cycloalkyl ring, or Z is optionally substituted carbocyclic aryl or optionally substituted heteroaryl group having from 1 to 3 rings, 5 to 5 members in each ring and from 1 to 3 heteroatoms;

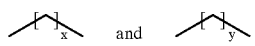

represent carbon chains which are independently unsubstituted or substituted with halogen, cyano, nitro, amino, mono or di($C_1$–$C_6$alkyl)amino, $C_2$–$C_6$alkenyl, $C_2$–$C_6$alkynyl, $C_1$–$C_6$alkoxy, trihalomethyl, trihalomethoxy, $C_1$–$C_6$alkyl, or $C_3$–$C_7$ cycloalkyl, x is 0, 1, 2, or 3; and y is 0, 1, 2, or 3.

2. A compound or salt according to claim 1, wherein:

R, $R_1$, $R_2$, A, B, C, D, and n are as defined in claim 1 and

Q is a phenyl, naphthyl, quinolinyl, thienyl, pyridyl, pyrimidinyl, pyrazinyl, oxazolyl, isoxazolyl, symmetrical or unsymmetrical oxadiazolyl, symmetrical or unsymmetrical thiadiazolyl, symmetrical or unsymmetrical triazolyl, pyrazolyl, furanyl, diazenyl, triazenyl, or triazolopyrazinyl group;

each of which is unsubstituted or substituted with up to three substituents independently selected from i) and ii) wherein i) is hydroxy, cyano, halogen, nitro, amino, mono or di($C_1$–$C_6$)alkylamino, $C_2$–$C_6$alkenyl, $C_2$–$C_6$alkynyl, $C_1$–$C_6$alkoxy, trihalomethyl, and trihalomethoxy;

ii) is $C_1$–$C_6$alkyl optionally containing heteroatoms and optionally substituted with one or more carbocyclic or heterocyclic group;

W is oxygen, nitrogen, sulfur, or $CR_7R^8$ where $R^7$ and $R^8$ are the same or different and represent hydrogen, $C_1$–$C_6$alkyl, or $R^7$ and $R^8$ may be taken together to represent a cyclic moiety having 3–7 carbon atoms;

Z is hydrogen, hydroxy, $C_1$–$C_6$alkoxy, $C_3$–$C_7$cycloalkyl, $C_3$–$C_7$cycloalkyl($C_{1-3}$alkoxy), amino, mono or di($C_1$–$C_6$alkyl)amino, a carbocyclic or heterocyclic group, or $NR^9COR^{10}$ where $R^9$ and $R^{10}$ are the same or different and represent hydrogen or $C_1$–$C_6$alkyl, or $R^9$ and $R^{10}$ may be joined to from a $C_3$–$C_7$ cycloalkyl ring, or Z is a phenyl, napthyl, quinolinyl, thienyl, thiazolyl, pyridyl, pyrimidinyl, imidazolyl, pyrazolyl, pyrazinyl, pyridizinyl, piperidinyl, oxazolyl, isoxazolyl, symmetrical or unsymmetrical thiadiazolyl, symmetrical or unsymmetrical triazolyl, symmetrical or unsymmetrical oxadiazolyl, pyrrolyl, furanyl, pyrimidinyl, diazenyl, triazenyl, 1,2,4-triazolone, 4,5-dihydroimidazolyl, or a 1,4,5,6-tetrahydropyrimidinyl group;

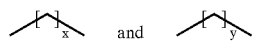

represent carbon chains which are unsubstituted or substituted with up to three groups independently chosen from halogen, cyano, nitro, amino, mono- or di($C_1$–$C_6$alkyl)amino, $C_2$–$C_6$alkenyl, $C_2$–$C_6$alkynyl, $C_1$–$C_6$alkoxy, trihalomethyl, trihalomethoxy, straight or branched chain $C_1$–$C_6$alkyl, or $C_3$–$C_7$cycloalkyl, and m is 0, 1, 2, or 3; and n is 0, 1, 2, or 3.

3. A compound or salt according to claim 2, wherein n is 1 and R, $R_1$, $R_2$, A, B, C, D, and Ar are as defined in claim 2.

4. A compound or salt according to claim 2, of the formula

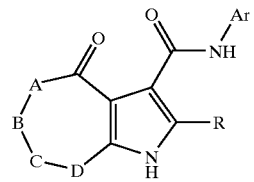

wherein R, Ar, and A, B, C, and D are as defined in claim 2.

5. A compound or salt according to claim 2, of the formula

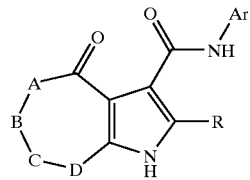

wherein R, Ar, are as defined in claim 2;
A is chosen from NR$_3$ and CR$_3$R$_{3''}$;
B is chosen from NR$_4$ and CR$_4$R$_{4''}$;
C is chosen from NR$_5$ and CR$_5$R$_{5''}$;
D is chosen from NR$_6$ and CR$_{6'}$R$_{6''}$; and not more than 2 members of the ring containing A, B, C, and D are nitrogen.

6. A compound or salt according to claim 2, of the formula

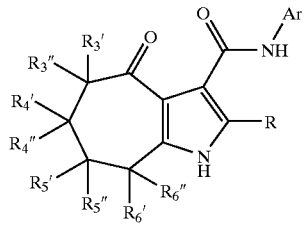

wherein R, Ar, R$_3$, R$_{3'}$R$_{3''}$, R$_4$, R$_{4'}$R$_{4''}$, R$_5$, R$_{5'}$R$_{5''}$, R$_6$, R$_{6'}$ and R$_{6''}$ are as defined in claim 2.

7. A compound or salt according to claim 2, of the formula

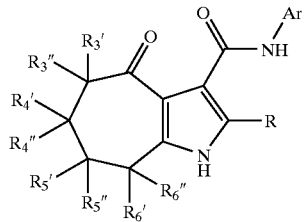

wherein R, R$_3$, R$_{3'}$R$_{3''}$, R$_4$, R$_{4'}$R$_{4''}$, R$_5$, R$_{5'}$R$_{5''}$, R$_6$, R$_{6'}$ and R$_{6''}$ are as defined in claim 2; and
Ar is phenyl, pyridyl or pyrimidinyl,
each of which is unsubstituted or substituted with up to three substituents independently selected from hydroxy, cyano, halogen, nitro, amino, mono or di(C$_1$–C$_6$)alkylamino, C$_2$–C$_6$alkenyl, C$_2$–C$_6$alkynyl, C$_1$–C$_6$alkyl, C$_1$–C$_6$alkoxy, trihalomethyl, or trihalomethoxy.

8. A compound or salt according to claim 2, of the formula

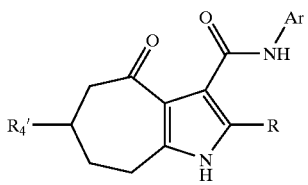

wherein R is as defined in claim 2; and
Ar is phenyl, pyridyl or pyrimidinyl,
each of which is unsubstituted or substituted with up to three substituents independently selected from hydroxy, cyano, halogen, nitro, amino, mono or di-(C$_1$–C$_6$)alkylamino, C$_2$–C$_6$alkenyl, C$_2$–C$_6$alkynyl, C$_1$–C$_6$alkyl, C$_1$–C$_6$alkoxy, trihalomethyl, or trihalomethoxy; and
R$_4$' is chosen from C$_3$–C$_7$cycloalkyl$_1$, C$_3$–C$_7$cyloalkyl$_1$ (C$_1$–C$_4$alkyl$_1$), heterocydoalkyl$_1$, heterocycloalkyl$_1$ (C$_1$–C$_4$alkyl$_1$), aryl$_1$, aryl$_1$(C$_1$–C$_4$alkyl$_1$), heteroaryl$_1$, and heteroaryl$_1$(C$_1$–C$_4$alkyl$_1$);
wherein each alkyl$_1$, cydoalkyl$_1$, heterocycloalkyl$_1$, aryl$_1$, and heteroaryl$_1$ is unsubstituted or substituted with one or more substituents selected from: hydroxy, oxo, halogen, amino, cyano, nitro, C$_1$–C$_6$alkyl, C$_1$–C$_6$alkoxy, amino(C$_1$–C$_6$alkyl); mono- or di-(C$_1$–C$_6$alkyl)amino, and mono- or di-(C$_1$–C$_6$alkyl)amino(C$_1$–C$_6$alkyl).

9. A compound or salt according to claim 2, of the formula

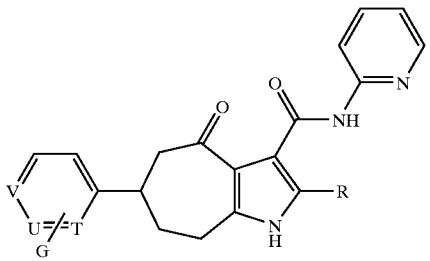

wherein
R is selected from hydrogen, halogen, methyl, and ethyl;
V, U, and T, independently represent N or CH; and
G represents up to 3 groups independently chosen from hydrogen, hydroxy, oxo, halogen, amino, cyano, nitro, C$_1$–C$_6$alkyl, C$_1$–C$_6$alkoxy, and mono- or di-amino (C$_1$–C$_6$alkyl).

10. A compound or salt according to claim 2, which is 6-(4-Fluoro-phenyl)-4-oxo-1,4,5,6,7,8-hexahydro-cyclohepta[b]pyrrole-3-carboxylic acid pyridin-2-ylamide.

11. A compound or salt according to claim 2, which is 4-(Pyridin-2-ylamino)-3,4,5,6,7,8-hexahydro-cyclohepta[b]pyrrole-3-carboxylic acid pyridin-2-ylamide.

12. A compound or salt according to claim 2, which is 6-Dimethylaminomethyl-4-oxo-3,4,5,6,7,8 hexahydro-cyclohepta[b]pyrrole-3carboxylic acid pyridin-2-ylamide.

13. A compound of the formula

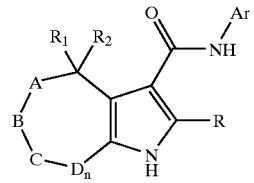

or a pharmaceutically acceptable salt, wherein:
R is selected from hydrogen, halogen, cyano, nitro, and amino;
R$_1$ is chosen from amino, fluoro, hydroxy, C$_1$–C$_6$ alkoxy, arylamino, heteroarylamino, aryloxy, or heteroaryloxy, and
R$_2$ is chosen from hydrogen, fluoro, C$_1$–C$_6$ alkyl, and aryl(C$_1$–C$_4$alkyl); or
R$_1$ and R$_2$ together represent an oxo group; or
R$_1$ and R$_2$ are joined to form a saturated, or partially unsaturated ring of from 4 to 8 members containing 1 or more heteroatoms independently chosen from N, S, and O;

n is 0, 1, or 2;

A is chosen from O, $NR_3$, and $CR_{3'}R_{3''}$;

B is chosen from O, $NR_4$, and $CR_{4'}R_{4''}$;

C is chosen from O, $NR_5$, and $CR_{5'}R_{5''}$;

D is independently chosen at each occurrence from O, $NR_6$, and $CR_{6'}R_{6''}$;

$R_3$, $R_4$, $R_5$, and $R_6$ are independently chosen at each occurrence from hydrogen, $C_1$–$C_6$ alkyl$_1$, $C_2$–$C_6$alkenyl$_1$, $C_2$–$C_6$alkynyl$_1$, $C_3$–$C_7$cycloalkyl$_1$, $C_3$–$C_7$cycloalkyl$_1$($C_1$–$C_4$alkyl$_1$), heterocycloalkyl$_1$, heterocycloalkyl$_1$($C_1$–$C_4$alkyl$_1$), hydroxy($C_1$–$C_6$ alkyl$_1$), amino($C_2$–$C_6$ alkyl$_1$), aryl$_1$, aryl$_1$($C_1$–$C_4$alkyl$_1$), heteroaryl$_1$, and heteroaryl$_1$($C_1$–$C_4$alkyl$_1$);

$R_{3'}$, $R_{3''}$, $R_{4'}$, $R_{4''}$, $R_{5'}$, $R_{5''}$, $R_{6'}$, and $R_{6''}$ are independently chosen at each occurrence from hydrogen, halogen, hydroxy, amino, cyano, nitro, oxo, $C_1$–$C_6$ alkyl, $C_1$–$C_6$ alkoxyl, $C_2$–$C_6$alkenyl$_1$, $C_2$–$C_6$alkynyl$_1$, $C_3$–$C_7$cycloalkyl$_1$, $C_3$–$C_7$cycloalkyl$_1$($C_1$–$C_4$alkyl$_1$), heterocydoalkyl$_1$, heterocycloalkyl$_1$($C_1$–$C_4$alkyl$_1$), halo($C_1$–$C_6$)alkyl$_1$, halo($C_1$–$C_6$)alkoxy$_1$ hydroxy($C_1$–$C_6$ alkyl$_1$), amino($C_1$–$C_6$ alkyl,), mono- or di($C_1$–$C_6$alkyl$_1$)amino, mono- or di($C_1$–$C_6$alkyl$_1$) amino($C_1$–$C_6$alkyl$_1$), aryl$_1$, aryl$_1$($C_1$–$C_4$alkyl$_1$), heteroaryl$_1$, and heteroaryl$_1$($C_1$–$C_4$alkyl$_1$);

wherein each alkyl$_1$, alkenyl$_1$, alkynyl$_1$, alkoxy$_1$, cycloalkyl$_1$, heterocycloalkyl$_1$, aryl$_1$, and heteroaryl$_1$ is unsubstituted or substituted with one or more substituents selected from: hydroxy, oxo, halogen, amino, cyano, nitro, $C_1$–$C_6$alkyl, $C_1$14 $C_6$alkoxy, and mono- or di-amino($C_1$–$C_6$alkyl); with the proviso that either $R_3$ or $R_3$' and $R_4$ or $R_4$' form an unsaturated, partially saturated, or saturated ring of from 5 to 7 members or $R_4$ or $R_4$' and $R_5$ or $R_5$' form an unsaturated, partially saturated, or saturated ring of from 5 to 7 members, wherein said unsaturated, partially saturated, or saturated ring contains 0, 1, or 2 heteroatoms independently chosen from S, O, or N and said unsaturated, partially saturated, or saturated ring is unsubstituted or substituted with up to 3 substitutents independently chosen from:

halogen, hydroxy, amino, cyano, nitro, oxo, $C_1$–$C_6$alkyl, $C_1$–$C_6$alkoxy, $C_2$–$C_6$alkenyl, $C_2$–$C_6$alkynyl, $C_3$–$C_7$cycloalkyl$_2$, $C_3$–$C_7$cycloalkyl$_2$($C_1$–$C_4$alkyl), heterocycloalkyl$_2$, heterocycloalkyl$_2$($C_1$–$C_4$alkyl), halo($C_1$6)alkyl, halo($C$-$C_6$)alkoxy, hydroxy($C_1C$ alkyl), amino($C_1$–$C_6$alkyl$_2$, mono- or di($C_1$–$C_6$alkyl$_2$) amino, aryl$_2$, aryl$_2$($C_1$–$C_4$alkyl), heteroaryl$_2$, and heteroaryl$_2$($C_1$–$C_4$alkyl);

wherein each cycloalkyl$_2$, heterocycloalkyl$_2$, aryl$_2$, and heteroaryl$_2$ is unsubstituted or substituted with one or more substituents selected from: hydroxy, oxo, halogen, amino, cyano, nitro, $C_1$–$C_6$alkyl, $C_1$–$C_6$alkoxy, and mono- or di-amino($C_1$–$C_6$alkyl);

Ar is a group of the formula

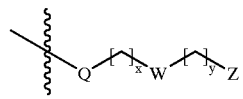

Q is an optionally substituted carbocyclic aryl or optionally substituted heteroaryl group having from 1 to 3 rings, 5 to 6 members in each ring and from 1 to 3 heteroatoms;

W is oxygen, nitrogen, sulfur, or $CR^7R_8$ where $R^7$ and $R^8$ are the same or different and represent hydrogen, $C_1$–$C_6$ alkyl, or $R^7$ and $R^8$ may be taken together to represent a cyclic moiety having 3–7 carbon atoms;

Z is hydrogen, hydroxy, $C_1$–$C_6$ alkoxy, $C_3$–$C_7$ cycloalkyl, $C_3$–$C_7$ cydoalkyl($C_1$–$C_4$alkoxy), amino, mono or di($C_1$–$C_6$alkyl)amino, or $NR^9COR^{10}$ where $R^9$ and $R^{10}$ are the same or different and represent hydrogen or $C_1$–$C_6$ alkyl, or $R_9$ and $R^{10}$ may be joined to from a $C_3$–$C_7$ cycloalkyl ring, or Z is optionally substituted carbocyclic aryl or optionally substituted heteroaryl group having from 1 to 3 rings, 5 to 6 members in each ring and from 1 to 3 heteroatoms;

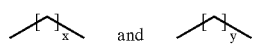

represent carbon chains which are independently unsubstituted or substituted with halogen, cyano, nitro, amino, mono or di($C_1$–$C_6$alkyl)amino, mono or di($C_1$–$C_6$alkyl)amino($C_1$–$C_6$alkyl), $C_2$–$C_6$alkenyl, $C_2$–$C_6$alkynyl, $C_1$–$C_6$alkoxy, trihalomethyl, trihalomethoxy, $C_1$–$C_6$alkyl, or $C_3$–$C_7$ cycloalkyl, and x is 0, 1, 2, or 3; and y is 0, 1, 2, or 3.

14. A compound or salt according to claim 13, wherein:

R, $R_1$, $R_2$, A, B, C, D, and n are as defined in claim 1 and

Q is a phenyl, naphthyl, quinolinyl, thienyl, pyridyl, pyrimidinyl, pyrazinyl, oxazolyl, isoxazolyl, symmetrical or unsymmetrical oxadiazolyl, symmetrical or unsymmetrical thiadiazolyl, symmetrical or unsymmetrical triazolyl, pyrazolyl, furanyl, diazenyl, triazenyl, or triazolopyrazinyl group;

each of which is unsubstituted or substituted with up to three substituents independently selected from i) and ii) wherein i) represents hydroxy, cyano, halogen, nitro, amino, mono or di($C_1$–$C_6$)alkylamino, $C_2$–$C_6$alkenyl, $C_2$–$C_6$alkynyl, $C_1$–$C_6$alkoxy, trihalomethyl, or trihalomethoxy;

ii) represents $C_1$–$C_6$alkyl optionally containing heteroatoms and optionally substituted with one or more carbocyclic or heterocyclic group;

W is oxygen, nitrogen, sulfur, or $CR^7R^8$ where $R^7$ and $R^8$ are the same or different and represent hydrogen, $C_1$–$C_6$alkyl, or $R^7$ and $R^8$ may be taken together to represent a cyclic moiety having 3–7 carbon atoms;

Z is hydrogen, hydroxy, $C_1$–$C_6$alkoxy, $C_3$–$C_7$cycloalkyl, $C_3$–$C_7$cycloalkyl($C_{1-3}$alkoxy), amino, mono or di($C_1$–$C_6$alkyl)amino, a carbocyclic or heterocylic group, or $NR^9COR^{10}$ where $R^9$ and $R^{10}$ are the same or different and represent hydrogen or $C_1$–$C_6$alkyl, or $R^9$ and $R^{10}$ may be joined to from a $C_3$–$C_7$, cycloalkyl ring, or Z is a phenyl, napthyl, quinolinyl, thienyl, thiazolyl, pyridyl, pyrimidinyl, imidazolyl, pyrazolyl, pyrazinyl, pyridizinyl, piperidinyl, oxazolyl, isoxazolyl, symmetrical or unsymmetrical thiadiazolyl, symmetrical or unsymmetrical triazolyl, symmetrical or unsymmetrical oxadiazolyl, pyrrolyl, furanyl, pyrimidinyl, diazenyl, triazenyl, 1,2,4-triazolone, 4,5- dihydroimidazolyl, or a 1,4,5,6-tetrahydropyrimidinyl group;

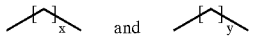

represent carbon chains which is unsubstituted or substituted with up to three groups independently chosen from halogen, cyano, nitro, amino, mono- or di($C_1$–$C_6$alkyl)amino, $C_2$–$C_6$alkenyl, $C_2$–$C_6$alkynyl, $C_1$–$C_6$alkoxy, trihalomethyl, trihalomethoxy, straight or branched chain $C_1$–$C_6$alkyl, or $C_3$–$C_7$cydoalkyl, and x is 0, 1, 2, or 3; and y is 0, 1, 2, or 3.

15. A compound or salt according to claim 14, wherein n is 1 and R, $R_1$, $R_2$, A, B, C, D, and Ar are as defined in claim 14.

16. A compound or salt according to claim 14, of the formula

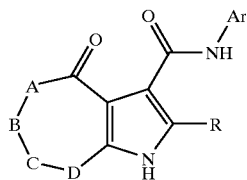

wherein R, Ar, and A, B, C, and D are as defined in claim 14.

17. A compound or salt according to claim 14, of the formula

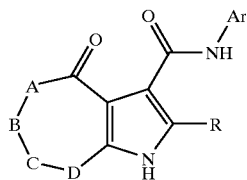

wherein R, Ar, are as defined in claim 14;

A is chosen from $NR_3$ and $CR_3R_{3''}$;

B is chosen from $NR_4$ and $CR_4R_{4''}$;

C is chosen from $NR_5$ and $CR_5R_{5''}$;

D is chosen from $NR_6$ and $CR_6R_{6''}$; and not more than 2 members of the ring containing A, B, C, and D are nitrogen.

18. A compound or salt according to claim 14, of the formula

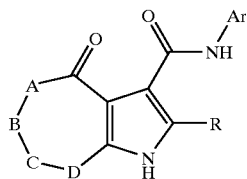

wherein R, Ar, $R_3$, $R_{3'}R_{3''}$, $R_4$, $R_{4'}R_{4''}$, $R_5$, $R_{5'}R_{5''}$, $R_6$, $R_{6'}$ and $R_{6''}$ are as defined in claim 14.

19. A compound or salt according to claim 14, of the formula

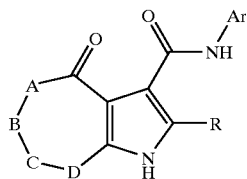

wherein R, $R_{3'}$, $R_{3''}$, $R_{4'}$, $R_{4''}$, $R_{5'}$, $R_{5''}$, $R_{6'}$ and $R_{6''}$ are as defined in claim 14; and Ar is phenyl, pyridyl or pyrimidinyl, each of which may be unsubstituted or substituted with up to three substituents independently selected from hydroxy, cyano, halogen, nitro, amino, mono or di($C_1$–$C_6$)alkylamino, $C_2$–$C_6$alkenyl, $C_2$–$C_6$alkynyl, $C_1$–$C_6$alkyl, $C_1$–$C_6$alkoxy, trihalomethyl, or trihalomethoxy.

20. A compound or salt according to claim 14, of the formula

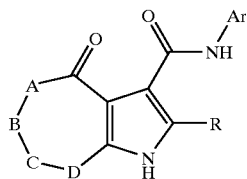

wherein:

R is as defined in claim 14;

$R_{5'}$, $R_{5''}$, $R_{6'}$, and $R_{6''}$ are independently chosen at each occurrence from hydrogen, halogen, hydroxy, amino, cyano, nitro, oxo, $C_1$–$C_6$ alkyl, $C_1$–$C_6$ alkoxy, $C_2$–$C_6$alkenyl, $C_2$–$C_6$alkynyl, halo($C_1$–$C_6$)alkyl, halo($C_1$–$C_6$)alkoxy, hydroxy($C_1$–$C_6$ alkyl), amino($C_1$–$C_6$ alkyl), mono- or di($C_1$–$C_6$alkyl)amino;

T', U', and V' are independently chosen from O, S, $CH_2$, and NH;

G' represents 0 to 3 substituents independently chosen from halogen, hydroxy, amino, cyano, nitro, oxo, $C_1$–$C_6$alkyl, $C_1$–$C_6$alkoxy, $C_2$–$C_6$alkenyl, $C_2$–$C_6$alkynyl, $C_3$–$C_7$cycloalkyl$_2$, $C_3$–$C_7$cycloalkyl$_2$($C_1$–$C_4$alkyl), heterocycloalkyl$_2$, heterocycloalkyl$_2$($C_1$–$C_4$alkyl), halo($C_1$–$C_6$)alkyl, halo($C_1$–$C_6$)alkoxy, hydroxy($C_1$–$C_6$ alkyl), amino($C_1$–$C_6$ alkyl$_2$, mono- or di($C_1$–$C_6$alkyl$_2$)amino, aryl$_2$, aryl$_2$($C_1$–$C_4$alkyl), heteroaryl$_2$, and heteroaryl$_2$($C_1$–$C_4$alkyl);

wherein each cycloalkyl$_2$, heterocycloalkyl$_2$, aryl$_2$, and heteroaryl$_2$ is unsubstituted or substituted with one or more substituents selected from: hydroxy, oxo, halogen, amino, cyano, nitro, $C_1$–$C_6$alkyl, $C_1$–$C_6$alkoxy, and mono- or di-amino($C_1$–$C_6$alkyl); and Ar is phenyl, pyridyl or pyrimidinyl, each of which is unsubstituted or substituted with up to three substituents independently selected from hydroxy, cyano, halogen, nitro, amino, mono or di($C_1$–$C_6$)alkylamino, $C_2$–$C_6$alkenyl, $C_2$–$C_6$alkynyl, $C_1$–$C_6$alkyl, $C_1$–$C_6$alkoxy, trihalomethyl$_1$, or trihalomethoxy.

21. A compound or salt according to claim 14 of the formula:

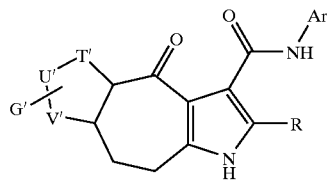

wherein R is chosen from hydrogen, halogen, methyl, and ethyl;

T', U', and V' are independently chosen from O, S, $CH_2$, and NH; and

G' represents up to 3 substituents independently chosen from halogen, hydroxy, amino, cyano, nitro, oxo, $C_1$–$C_6$alkyl, $C_1$–$C_6$alkoxy, $C_2$–$C_6$alkenyl, $C_2$–$C_6$alkynyl, $C_3$–$C_7$cycloalkyl$_2$, $C_3$–$C_7$cycloalkyl$_2$($C_1$–$C_4$alkyl), heterocycloalkyl$_2$, heterocycloalkyl$_2$($C_1$–$C_4$alkyl), halo($C_1$–$C_6$)alkyl, halo($C_1$–$C_6$)alkoxy, hydroxy($C_1$–$C_6$ alkyl), amino($C_1$–$C_6$ alkyl$_2$, mono- or di($C_1$–$C_6$alkyl$_2$)amino, aryl$_2$, aryl$_2$($C_1$–$C_4$alkyl), heteroaryl$_2$, and heteroaryl$_2$($C_1$–$C_4$alkyl);

wherein each cycloalkyl$_2$, heterocycloalkyl$_2$, aryl$_2$, and heteroaryl$_2$ is unsubstituted or substituted with one or more substituents selected from: hydroxy, oxo, halogen, amino, cyano, nitro, $C_1$–$C_6$alkyl, $C_1$–$C_6$alkoxy, and mono- or di-amino($C_1$–$C_6$alkyl).

22. A compound or salt according to claim 14, of the formula

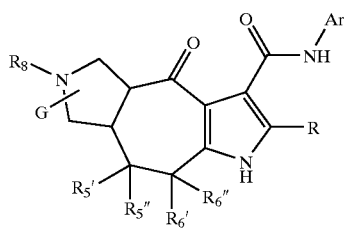

wherein R is chosen from hydrogen, halogen, methyl, and ethyl;

$R_5{'}$, $R_5{''}$, $R_6{'}$, and $R_6{''}$ are independently chosen at each occurrence from hydrogen, halogen, hydroxy, amino, $C_1$–$C_6$ alkyl, $C_1$–$C_6$ alkoxy, trihalomethyl, and trifluoromethyoxy; and G represents 0 to 3 substituents independently chosen from halogen, hydroxy, amino, cyano, nitro, oxo, $C_1$–$C_6$alkyl, $C_1$–$C_6$alkoxy, $C_2$–$C_6$alkenyl, $C_2$–$C_6$alkynyl, $C_3$–$C_7$Cycloalkyl$_2$, $C_3$–$C_7$cycloalkyl$_2$($C_1$–$C_4$alkyl), heterocycloalkyl$_2$, heterocycloalkyl$_2$($C_1$–$C_4$alkyl), halo($C_6$)alkyl, halo($C_1$–$C_6$)alkoxy, hydroxy($C_1$–$C_6$ alkyl), amino($C_1$–$C_6$ alkyl$_2$, mono- or di($C_1$–$C_6$alkyl$_2$)amino, aryl$_2$, aryl$_2$($C_1$–$C_4$alkyl), heteroaryl$_2$, and heteroaryl$_2$($C_1$–$C_4$alkyl);

wherein each cycloalkyl$_2$, heterocycloalkyl$_2$, aryl$_2$, and heteroaryl$_2$ is unsubstituted or substituted with one or more substituents selected from: hydroxy, oxo, halogen, amino, cyano, nitro, $C_1$–$C_6$alkyl, $C_1$–$C_6$alkoxy, and mono- or di-amino($C_1$–$C_6$alkyl); and $R_6$ is chosen from hydrogen and $C_1$–$C_6$alkyl.

23. A compound or salt according to claim 22, wherein Ar represents phenyl, pyridyl, or pyrimidinyl each or which may be unsubstituted or substituted with 1, 2, or 3, substituents chosen from hydroxy, halogen, amino, nitro, cyano, $C_1$–$C_6$ alkyl, $C_1$–$C_6$alkoxy, trihalomethyl, trihalomethoxy, amino($C_1$–$C_6$ alkyl), mono- or di($C_1$–$C_6$ alkyl)amino, and mono- or di($C_1$–$C_6$ alkyl)amino($C_1$–$C_6$ alkyl).

24. A compound or salt according to claim 14, which is: 4-Oxo4,4a,5,6,7,7a,8,9-octahydro-1H-1,6-diazacyclopenta[f]azulene-3-carboxylic acid pyridin-2-ylamide.

25. A compound or salt according to claim 14, which is 6Benzyl-4-oxo-4,4a,5,6,7,7a,8,9-octahydro-1H-1,6-diazacyclopenta[f]azulene-3-carboxylic acid pyridin-2-ylamide.

26. A pharmaceutical composition comprising an effective amount of a compound according to claims 1 or 13 with at least one pharmaceutically acceptable carrier or excipient.

27. The pharmaceutical composition of claim 26 wherein the pharmaceutical composition is formulated as an injectable fluid, a pill, a capsule, a syrup, or a transdermal patch.

28. A packaged pharmaceutical composition comprising the pharmaceutical composition of claim 26 in a container and instructions for using the composition to treat a patient suffering from anxiety, depression, a sleep disorder, attention deficit disorder, or Alzheimer's dementia.

29. A compound according to claim 1 or 13 wherein in an assay of $GABA_A$ receptor binding the compound exhibits an $K_i$ of 1 micromolar or less.

30. A compound according to claim 1 or 13 wherein in an assay of $GABA_A$ receptor binding the compound exhibits an $K_i$ of 100 nanomolar or less.

31. A compound according to claim 1 or 13 wherein in an assay of $GABA_A$ receptor binding the compound exhibits an $K_i$ of 10 nanomolar or less.

* * * * *